United States Patent [19]

Shohet

[11] Patent Number: 5,420,108
[45] Date of Patent: May 30, 1995

[54] METHOD OF CONTROLLING DIABETES MELLITUS

[76] Inventor: Isaac H. Shohet, 70-34 Kissena Blvd., Flushing, N.Y. 11367

[21] Appl. No.: 943,176

[22] Filed: Sep. 14, 1992

[51] Int. Cl.$^6$ .............. A61K 38/28; C07K 5/00; C07K 7/00; C07K 14/62
[52] U.S. Cl. ............................. 514/3; 514/4; 514/12; 530/300; 530/303; 530/324
[58] Field of Search ............... 514/3, 4, 12; 530/300, 530/303, 324

[56] References Cited

U.S. PATENT DOCUMENTS

| | | | |
|---|---|---|---|
| 3,655,873 | 4/1972 | Duffy | 128/214 |
| 4,073,292 | 2/1978 | Edelman | 128/214 |
| 4,206,755 | 6/1980 | Klein | 128/214 |
| 4,362,719 | 12/1982 | Cavazza | 424/178 |
| 4,371,374 | 2/1983 | Cerami et al. | 422/57 |
| 4,493,793 | 1/1985 | Chu | 424/88 |
| 4,571,391 | 2/1986 | Riley et al. | 514/4 |
| 4,731,726 | 3/1988 | Allen, III | 364/416 |
| 4,761,287 | 8/1988 | Geho | 424/450 |
| 4,863,896 | 9/1989 | Geho et al. | 514/3 |
| 5,019,974 | 5/1991 | Beckers | 364/413.02 |
| 5,114,844 | 5/1992 | Cohen et al. | 435/7.21 |
| 5,122,362 | 6/1992 | Phillips et al. | 424/9 |
| 5,124,360 | 6/1992 | Larner et al. | 514/738 |

OTHER PUBLICATIONS

Service et al., *JAMA*, vol. 222, No. 3, pp. 294-298, Oct. 16, 1972.
Daniel W. Foster, MD "Insulin Resistance—A Secret Killer?", New England Journal of Medicine, Mar. 16, 1989, vol. 320, No. 11, pp. 733-734.
Ivana Zavaroni, et al "Risk Factors for Coronary Artery Disease in Healthy Persons with Hyperinsulinemia and Normal Glucose Tolerance", New England Journal of Medicine, Mar. 16, 1989, vol. 320, No. 11, pp. 702-705.
Luciano Rossetti, MD "Glucose Toxicity", Diabetes Care, vol. 13, No. 6, Jun. 1990, pp. 610-630.
Philip E. Cryer, et al "Hypoglycemia in IDMM", Diabetes, vol. 38, No. 9, Sep. 1989, pp. 1193-1199.

*Primary Examiner*—Jill Warden
*Assistant Examiner*—A. M. Davenport

[57] ABSTRACT

The use of precise dosages of insulin-plus-sugar in a method of controlling and/or treating diabetes is disclosed, including the steps of frequently testing both the blood sugar level and the urine sugar level of the diabetic patient; and administering insulin and/or sugar as required by the results of the blood and urine sugar tests. The amount of insulin and/or sugar administered is reviewed daily and modifications are made on a daily basis such that the patient over time will need little or no insulin. The present invention is also related to a method for controlling the out-of-control diabetic patient and to a method for reversing the negative effects already caused by diabetes. This method also avoids the side effects of insulin use such as hypoglycemia and hyperinsulinemia.

19 Claims, No Drawings

METHOD OF CONTROLLING DIABETES MELLITUS

The present invention relates to a method of controlling diabetes in diabetic patients. Specifically, it relates to a method of using insulin-plus-sugar in the control of diabetes. More specifically, it relates to the utilization of sugar and insulin in precise dosages to reduce or eliminate the dependency of diabetic patients on administered insulin and/or any other antidiabetic agents, referred to in the art as "the pill".

While exercise and weight reduction are beneficial and complementary, the above-mentioned results are achieved without weight loss or change in exercise habits. However, at any time during the course of diabetic care, weight loss and exercise are useful and will expedite the realization of the above-mentioned results and additionally will cushion against flare-ups that may result from physical and emotional stresses.

BACKGROUND OF THE INVENTION

Insulin has been used to control diabetes in diabetic patients since the discovery of insulin some 70 years ago and is prescribed in many ways. In recent years, insulin has come to be prescribed in one of two different ways to diabetic patients:

1. The more commonly used conventional method uses injections of (a) long-acting or (b) mixed short-acting and long-acting insulins once or twice daily.

This method has not been deemed satisfactory for the control of diabetes mellitus because hypoglycemias continued to occur. The insulin dosage has often tended to increase over time and vascular complications of diabetes tended to appear prematurely with resulting chronic disabilities and premature death. Good control, which is defined by many clinicians as normal or near normal blood glucose levels especially before breakfast but also before and after meals, was rarely achieved by this method.

2. In an intensive method, which hoped to correct the deficiencies of the conventional method, either (a) mixed long-acting insulin plus regular insulin (b) and/or regular insulins are given 3 to 5 times a day with more intensive testing and professional encounters than with the conventional method. The goal of such therapy is to approximate the natural non-diabetic state of insulin secretion. The insulin dosage is adjusted up and down according to a set algorithm based on the results of frequent blood tests. The patient and the professional team participate in such testing.

To date, no unequivocal improvement in results has been demonstrated and severe hypoglycemias have occurred even more frequently in such patients.

In recent years, blood sugar tests have been utilized to access the adequacy of insulin treatment and to adjust the insulin dosage accordingly.

Urine tests for glucose have lost their prior prominence because they gave rough estimates of the blood glucose values and were therefore deemed as inadequate methods for monitoring diabetes. Urine tests were discarded by many diabetologists.

The diet is always an important and necessary part in the control of diabetes. In recent years, the diet consisted of a lower total fat and lowered total saturated and polyunsaturated fats. A higher carbohydrate intake was needed to meet calorie requirements since the proteins were fixed at 15-20% of the total calories. Monounsaturated fats were given more prominence in order to cut down on the carbohydrates because carbohydrates in short term studies have tended to increase the triglyceride levels and to lower the levels of high density lipoproteins which carry the "good cholesterol".

Generally, the diabetic diet is divided into 3 meals and 2-4 snacks. Snacks are given between meals and at bedtime, as part of the total prescribed calories, in order to prevent hypoglycemias. The diet is also used for weight reduction, which is beneficial to the diabetic. However, the success of diet therapy is limited in scope and duration and only about 20% derive more lasting benefits from it.

In all of these known methods of controlling diabetes, iatrogenic hypoglycemias have continued to occur and the vascular complications of diabetes have not been prevented, arrested or reversed. Besides, the set goals of normalization of the elevated plasma glucose were achieved only rarely.

As is known and as used in the present application, the following definitions apply:

Type 1 diabetes, which used to be called juvenile onset diabetes, occurs in 3-5% of diabetics. Also, up to 10% of type 2 insulin-requiring diabetics may actually be adult-onset type 1.

Type 2 diabetes comprises 80-95% of all diabetics. This type of diabetes used to be called adult or maturity onset diabetes.

Secondary diabetes, in which the diabetes is a secondary manifestation of another ailment, comprises the rest.

DESCRIPTION OF THE PRIOR ART

In the June 1990 issue of "Diabetes Care", Rosetti et al (the entire disclosure of which is incorporated herein by reference), it states:

Unfortunately, there is compelling evidence that hyperinsulinemia may be associated with accelerated atherosclerosis, hypertension, hypertriglyceridemia and reduced high density lipoprotein cholesterol. Insulin per se is also capable of causing insulin resistance. This presents clinicians with a major therapeutic dilemma particularly in type 2 diabetic subjects. Do they attempt to normalize the blood glucose level, knowing that hyperglycemia is associated with microvascular (nephropathy, retinopathy, neuropathy) complications while recognizing that hyperinsulinemia per se may promote a more atherogenic profile?. A solution to this difficult question is not at hand.

In this regard, it is fair to say that the insulin treatment of Rosetti et al often produced iatrogenic hyperinsulinemia in such patients.

In an editorial in the New England Journal of Medicine on Mar. 16, 1989 (the entire disclosure of which is incorporated herein by reference), Daniel W. Foster M.D., speaking of hyperinsulinemia, stated:

Finally, if Syndrome X can be produced by the rather mild insulin resistance and hyperinsulinemia found in the apparently normal persons described by Zavaroni et al, it will be an alarming thing for diabetologists. They rarely normalize the elevated plasma glucose levels caused by the insulin deficiency or insulin resistance in their patients with diabetes mellitus, and their efforts often produce hyperinsulinemia.

In the September 1989 issue of "Diabetes" (the entire disclosure of which is incorporated herein by reference), an international panel stated: "The ultimate challenge is to learn to prevent iatrogenic hypoglycemia." These problems still remain unsolved.

U.S. Pat. No. 5,019,974, to Beckers, U.S. Pat. No. 4,206,755, to Klein and U.S. Pat. No. 4,731,726, to Allen, III all describe computer technologies that would assist an attending physician in carrying out his instructions to his patients in the areas of testing and treatment. The attending physician is in charge and he determines the treatment according his own judgement. The computer does not prescribe for the patient, the doctor does.

U.S. Pat. No. 4,362,719, to Cavazza, U.S. Pat. No. 5,124,360, to Larner et al, U.S. Pat. No. 4,571,391, to Riley et al, U.S. Pat. No. 4,761,287, to Geho and U.S. Pat. No. 4,863,896, to Geho et al, relate to dietary and other supplementation for the control of diabetes. The U.S. patents to Geho also describe a mode of insulin delivery in laboratory animals. U.S. Pat. No. 4,371,374, to Cerami et al, discloses the use of glycosylated amino acids and peptides in the urine as a measure of long term assessment of diabetic control. U.S. Pat. No. 5,122,362, to Phillips et al, describes a new modified glucose tolerance test for the diagnosis of diabetes.

Many of these U.S. patents (which are each incorporated herein by reference) describe inventions which are personally currently in use in one form or another to assist the treating physician in the manners described in the patents. However, none of these references disclose or suggest a manner for the treatment of an actual diabetic patient or for the use of a insulin-plus-sugar treatment in the control of diabetes.

BRIEF DESCRIPTION OF THE PRESENT INVENTION

One object of the present invention is to provide a method of using insulin-plus-sugar in precise dosages in diabetics with the object of reducing both the insulin and the sugar requirements of the patient to zero or near zero, most commonly in about 1–2 months.

Another object of the present invention is to provide a method of controlling the glucose level in diabetic patients without inducing hypoglycemias.

In the present process, iatrogenic hyperinsulinemia is also prevented and pre-existing vascular and neuropathic complications tend to reverse significantly.

In its broadest form, the method of the present invention comprises the treatment of diabetes mellitus using 2 generic substance, namely insulin and sugar prescribed in precise amounts based on the results of frequent urine and blood glucose tests, to achieve zero or near zero insulin or pill requirements most commonly in as brief as period of time as 1–2 months.

The present invention overcomes the problems of known treatments for diabetes, such as those discussed above. Important advantages of the present invention include:

1. The ability to reverse an out-of-control diabetic to a compensated state without requiring weight loss, change in exercise habits or change in life style.
2. The complete prevention of hypoglycemia of any severity, even in those diabetics who were already experiencing hypoglycemia under someone else's care.
3. Since insulin dosages are either precisely sufficient for the patient's need on any one day or about one unit less per dose while on the insulin-plus-sugar therapy of the present invention, iatrogenic hyperinsulinemia is prevented.
4. Patients with pre-existing vascular and neuropathic complications frequently exhibit a significant reversal of these complications in a matter of weeks.
5. Nearly any diabetic can easily learn to follow the present method. Peace of mind and preserved quality of life flow from the simplicity and predictability of this method.
6. The cost of diabetic care under this method is dramatically reduced.

DETAILED DESCRIPTION OF THE PRESENT INVENTION

As discussed above, type 2 diabetes is the most common. Therefore, the discussion and examples refer to this type of diabetes. However, the use of the present invention is not limited to type 2 diabetes. That is, the present invention can be used also with type 1 diabetic patients and patients having secondary diabetes, as well as with patients having any other types of diabetes which may be known.

Any diabetic, regardless of the degree of his diabetic control can be treated by the present invention. The diet generally prescribed within this invention should avoid fried and greasy foods and foods containing sugar or honey. No between meal snacks except as discussed below are permitted. The patient should at least try not to gain weight. Losing weight is recommended.

Prior to the present invention, it has become a very common practice to control diabetes based solely on the results of the blood glucose tests. The present inventor has found that while blood tests serve an important and necessary role in controlling and treating diabetes, they do not give all the necessary data needed for day-to-day diabetes control. However, when the blood sugar tests are combined with urine sugar tests, these deficiencies are overcome.

The patient is instructed to test his blood and urine seven times a day as follows for sugar levels:

Before meals (3 times a day);

2 hours after each meal (3 times a day); and

At bedtime (1 time a day).

If the patient can not do all seven blood tests in a day, he is encouraged to conduct as many blood tests as possible.

Sometimes, especially early in the treatment, seven or more blood glucose tests a day are required if the urine sugar tests consistently show 2% results, the maximum reading on the usual dipstick. Here, the persistence of very high blood sugar readings would dictate a more rapid increase in insulin dosages.

Some patients whose insulin intake is already down to zero may still exhibit elevated blood glucose values, elevated hemoglobin $A_{IC}$ (HgA$_{IC}$) or elevated triglycerides while the urine sugars remain negative. These situations may be seen in the elderly, in those with impaired kidney function or in those diabetics whose prior insulin or pill therapy under somebody else's care required unnecessarily high dosages of insulin for months or years. In these situations, 2–3 units of regular insulin before breakfast and occasionally 2–3 units before supper as well may suffice to adequately control these elevated values.

Similarly, the present inventor has found that insulin alone is not sufficient to adequately treat diabetes.

Instead, the present inventor has found that when a combination of insulin-plus-sugar is prescribed in precise amounts and adjusted daily based on both blood and urine tests for sugar, not only is hypoglycemia prevented but also the need for continued insulin can be steadily and predictably reversed. That is, a zero or near zero insulin requirement with normoglycemia can be achieved. This result is consistently evident with type 2 diabetics whose diabetes was diagnosed within the preceding six months or so regardless of their prior treatment or state of control. In addition, pre-existing diabetic vascular and neuropathic complications tend to be reversed significantly.

New orders for insulin and sugar are given every day according to the results of the blood and urine tests. Each patient is started at an insulin dosage that is below anticipated requirements in order to avoid any hypoglycemias. A typical initial insulin order in a diabetic spilling sugar throughout the 24 hours a day is as follows:

| | |
|---|---|
| 8–10 u NPH (a form of art, also known as isophane insulin suspension + 8–15 u regular | ½ an hour before breakfast; |
| 4–6 u regular | ½ an hour before lunch; and |
| 6–8 u NPH + 6–8 u regular | ½ an hour before supper. |

The patient is also prescribed sugar, in the form of juice, fruit, sodas, hard candies, and the like. A typical initial sugar order is as follows: If the urine test is negative, 2 hours after breakfast, 2 hours after lunch, 2 hours after supper or at bedtime the patient is instructed to take 2 ounces of juice, which is equal to 6 grams of sugar or 1½ level teaspoons of sugar. If the urine test is 1/10% at these same times (the color next to negative on the urine test dipstick), then 1 ounce of juice is prescribed. No juice is given if the urine test is higher than 1/10%.

No snacks are allowed at any time. The juice, as discussed above, is the only between meal order and then only when that urine test is negative or 1/10%.

In some patients whose diabetes is very severe at presentation, the insulin requirement will often peak at a very high level. In such instances, when improvement begins, the insulin requirement often drops rapidly. In order to avoid hypoglycemias in such patients, the sugar order is increased as follows:

| 2 hours after meals and at bedtime | |
|---|---|
| If the urine test is negative | 8 ounces of juice; |
| If the urine test is 1/10% | 4 ounces of juice; |
| If the urine test is ¼% | 2 ounces of juice; and |
| If the urine test is ½% | 1 ounce of juice. |

Lesser amounts of juice are prescribed if the insulin requirements are higher than average but not extremely high.

The corresponding blood sugar levels are obviously high since sugar appears in the urine only after the blood sugar level exceeds the renal threshold for sugar. This may occur at a blood glucose level of 160–180 mg or higher, a hyperglycemic level. Consequently, the more sugar that spills into the urine, the higher the corresponding blood sugar level.

The blood sugar reflects the level of sugar in the blood at any one particular moment in time. However, the blood sugar cannot interpret the trend (what is to come next), except in retrospect after evaluating up to 3 days of blood test results. On the other hand, as the sugar level in the urine begins to drop, a downward trend is predictably under way, even though the blood sugar level may still be high. Sugar supplementation now becomes necessary in order to avoid the possibility of a steep, rapid drop in the blood sugar level to possibly hypoglycemic levels before the next meal, especially considering the large amount of remaining available insulin.

As the insulin requirement of the diabetic patient drops, the orders for juice also drop, and when the insulin requirements are low and the risk of hypoglycemia becomes more remote, the sugar order drops to 1 ounce when the urine test is negative and none when the urine test is 1/10%. At a level of 2–3 units of insulin, no juice is required. Although sugar, specifically juice, is given to the patient in the discussion herein, it is contemplated that any food which would affect the sugar levels in the blood and urine can be administered. It would be clear to one skilled in the art from this disclosure how much of any such food should be prescribed to achieve the desired result.

As the insulin requirement drops, these drops in the sugar supplementation are necessary in order to prevent the supplementation itself from becoming a source of hyperglycemia in the patient.

NPH action covers a time frame of all 3 meals. Regular insulin covers a time frame of more than one meal. Insulin adjustments take this overlap into consideration. Any and all types of insulins can be used, as long as their action characteristics are considered in determining the amount and timing of the insulins to be given. Regular insulin and NPH are merely examples of types of insulin which can be used in the present invention. From this disclosure, it would be clear to one skilled in the art how to modify the amount of insulin necessary when different types of insulin are utilized. It is contemplated that any insulin presently available, any modifications of insulin that may be available in the future and any insulin substitutes which are developed can be used in the present invention.

In the usual case, each insulin dose is adjusted according to the corresponding test result as summarized below:

| Test time | Insulin involved |
|---|---|
| Before breakfast | The evening NPH |
| 2 hours after breakfast | The morning regular |
| Before lunch | The morning regular |
| 2 hours after lunch | The before lunch regular and the morning NPH |
| Before supper | The morning NPH and the before lunch regular |
| 2 hours after supper | The before supper regular and the morning NPH |
| Bedtime | The before supper regular and the evening NPH |

However, some fine-tuning is required because of overlap.

The amount of juice also has to be precise in order not to underestimate or overestimate the need therefor, thus avoiding hypoglycemia or hyperglycemia, respectively.

Anytime juice is taken, the insulin dosage that covers that time of day should be reduced by 1–2 units on the next day. This is necessary because:

1. The counter-regulatory hormones excess, the insulin antagonist, has now been eliminated with the elimination of the stress of uncontrolled diabetes.
2. Insulin action becomes greatly enhanced because insulin resistance is now reduced by the elimination of hyperglycemia and the elevated counter-regulatory hormones.
3. The suppressed and exhausted pancreas caused by the previous hyperglycemia and the lack of diabetic control has now been revitalized.
4. Adequate insulinization has controlled the excessive hepatic glucose production.
5. In new type 2 diabetics and in any diabetic who has a residual ability of the pancreas to produce insulin (as measured by the C-peptide blood levels), pancreatic insulin production can be made to increase. In type 2 diabetics, especially of recent onset, increased production of insulin can be stimulated to match the need if the extra demand is made small (1–2 units early in the treatment and only 1 unit later on), much like training a muscle to a greater strength. An awakened pancreas can produce the needed units usually in 1 day, but may take up to 3 days.

Since the urine tests are now negative nearly all the time, the drop in insulin requirements will be steady and predictable and a zero requirement or near zero requirement will generally be reached in a month or two.

To summarize, the amount of insulin prescribed has to be calculated to within one unit of the need every day. The amount of juice has to be calculated to within one ounce of the need. Both have to be precise at all times to avoid both insulin-induced hypoglycemia and juice-induced hyperglycemia. One extra unit of insulin can create hypoglycemia and an extra ¾ of a teaspoon of sugar can create hyperglycemia. In this regard, hypoglycemia is defined as any drop below basal levels. This chemical hypoglycemia is contrasted with symptomatic hypoglycemia which is more dependent on the actual blood sugar value (range from hypoglycemic to slightly hyperglycemic values). However, this chemical hypoglycemia can still be sufficient to foul up the diabetic control for up to 3 days.

Hypoglycemia is damaging in a number of ways. Severe hypoglycemia can kill or damage the brain. It cuts insulin action both in depth and duration by stimulating counter-regulatory hormones that act to prevent a further dip in the blood sugar and to raise the blood sugar, sometimes to hyperglycemic values. Furthermore, when the tests of blood or urine are infrequent or wrongly timed, rebound hyperglycemia may not be uncovered as such and the unaware physician may instead increase the insulin in order to treat the newly created hyperglycemia. Thus, a vicious cycle may be created and the insulin dose may reach 150 u/day or more.

Additionally, when snacks are given routinely, without regard to the immediate need of the patient, they can prevent the blood sugar level from dropping down sufficiently and speedily and may thus dictate the need for higher insulin dosages. Since near normoglycemia is also demanded by some specialists in the field, here again, diabetic control is affected and a cycle of fluctuating blood sugars and hyperinsulinemia is created with their known toxicities and proclivities to vascular complications.

A precise insulin-plus-sugar dosage, prescribed according to the present invention, would instead make the diabetes progressively milder and would actually reverse it to a compensated state in 1–2 months, i.e. independent of both insulin and antidiabetic pills. This is accomplished without the benefit of any weight loss or change in exercise habits. However, if subsequent reduction in insulin demand is created by weight loss and exercise, then an insulin reserve capacity will have been created and even major stresses caused by illness or injury can often be met without the need, even temporary, for insulin or pill therapy.

Insulin-Plus-sugar Treatment of Diabetes Mellitus-A

Detailed Description

The following describes an insulin-plus-sugar method of treating type 2 recently diagnosed diabetes. This method can be applied to any type of diabetes of any duration. Six stages of the method are described below:

Stage I

In the usual case, as described herein, smaller-than-required dosages of insulin are started, in the form of NPH+regular ½ hour before breakfast, regular alone ½ hour before lunch and NPH+regular ½ hours before supper.

Insulin is increased daily, usually by 2–3 units/dose in accordance with blood and urine sugar tests results until the maximum requirement is reached. However, insulin increases per dose may reach 5 or more units if a speedier reduction in the blood and urine sugar values is required.

Early in this stage, when the urine sugar tests read a consistent 2% (the maximum on the usual dipstick, such as Diastix), the blood sugar will reveal the rate of decrease in the glycemic levels and therefore help determine the rate of increase in insulin dosages.

This stage ends, and the peak insulin requirement is reached, when the between meals or bedtime urine sugar tests show negative or 1/10% on the Diastix dipstick. Other types of testing are also satisfactory. Therefore, no sugar supplementation is required at this stage unless the total daily insulin requirement at its peak is high. About 80 Units daily is high but a lesser amount may also be considered high if the individual diabetic shows a higher degree of sensitivity to insulin.

In stage I, the blood sugar tests are all high. Occasionally however, the blood sugar values are not so elevated when the urine sugar values still show high readings. In such a case, both blood and sugar readings have to be considered in assessing the trend and the blood sugar values, not he urine sugar values, will become the trend-setter and insulin dosages would be decreased despite the persistence of relatively high urine sugar values.

If the peak insulin requirement is 140 units or more, the schedule of 8 ounces of juice when negative, 4 ounces when 1/10%, 2 ounces when ¼% and 1 ounce when ½% will apply. No juice is given when the test is higher than ½%.

If the peak insulin requirement is between 80 and 139 units, the schedule of 4 ounces of juice when negative, 2 ounces when 1/10% and 1 ounce when ¼% will apply. No juice is given when the urine glucose test is higher than ¼%.

The juice supplementation of 2 ounces when negative and 1 ounce when 1/10% will apply if the insulin requirement at its peak is less than 80 units. This level of juice supplementation will start at stage II, as the definition of stage I suggests.

The peak insulin requirement that would trigger higher or lower schedules of sugar supplementation may vary substantially in the individual diabetic patient depending on the degree of the patient's resistance or sensitivity to insulin.

What is disclosed here is what is observed in the usual case.

Stage I usually lasts 4–5 days, i.e., the peak insulin requirement is reached in 4–5 days. However, it may range from 1–3 days.

A one-day stage I occurs when the first day insulin dosages produce a negative or 1/10% urine sugar test at any time between meals or at bedtime. A 30 day stage I occurs when insulin is increased cautiously because of cardiac or other associated conditions that may be harmed by hypoglycemia caused by overinsulinization.

Stage II

This stage starts when the peak total daily insulin dosage is reached. At this stage, urine sugar test results range from zero to 2% on the Diastix dipstick.

Stage II is characterized by an uneven improvement in diabetic control within the 24 hour period. This would dictate that each insulin dosage taken before the meal be individually adjusted up and down or unchanged as required by the test results. The total daily dosage, however, may be higher or lower or may stay the same.

This stage may be skipped altogether or it may last several days. Sugar supplementation will be given as needed when the urine test between meals or at bedtime reads negative or 1/10%.

Stage III

Stage III marks the beginning of a steady drop in insulin requirements. While the urine sugar tests may still range from zero to 2%, the insulin requirements per day will each day be lower than the day before. The blood sugars will show corresponding improvements even though they may lag somewhat in that they may still be slightly high when the urine has already turned negative. Sugar supplementation will become more frequent.

Stage III may also be skipped altogether or may last a week or longer.

Stage IV

Stage IV is characterized by further improvements in the blood and urine sugar levels. 2% sugar in the urine will be infrequent. Negative tests will become increasingly more frequent and sugar supplementation will become the rule rather than the exception. Insulin requirements will drop daily, sometimes at an accelerated rate.

Stage IV may also be skipped or may last 2 weeks or longer.

Stage V

Stage V is marked by nearly uniform negative urine tests and a corresponding normalization of the blood sugar levels. Sugar supplementation will almost always be needed. Insulin dosages are nearly always decreased daily, sometimes at an accelerated rate. This stage will be maintained until the total insulin requirements drop to less than 20 units/day still given in 2–3 divided doses of regular and/or mixed insulins. Thus, each dose of insulin is too small to cause either hypoglycemia or iatrogenic hyperinsulinemia considering the fact that 1 ounce of juice is still given when the urine test is negative between meals and/or at bedtime.

For this reason, insulin reductions will be continued at a slower rate even though nearly all urine tests continue to be negative and the blood glucose levels continue to be normal or near normal.

This stage reminds the diabetic patient that he is still a diabetic, albeit a compensated one, and that continued vigilance will be required for life.

At this stage and thereafter, weight loss will be more forcefully encouraged because it will help create an insulin reserve capacity that would cushion against flare-ups that may result from stresses such as those caused by illness or injury.

At this stage, exercise is fraught with fewer complications but its benefits are impressive. Many cardiac risk factors are improved by exercise. The blood sugars also improve further. The diabetic feels more energetic. It contributes to an improved self-image and life style.

Stage VI is continued until all insulin and sugar requirements are reduced to zero or near zero.

Stage VI may also be skipped or may be allowed to run for several months depending on the motivation of the diabetic patient.

The following Examples further illustrate the present invention. These Examples are presented as illustrations of the present invention and are not intended to limit the scope of the disclosure thereof.

EXAMPLE 1

| Date | |
|---|---|
| 07/06/92 | First saw this patient today. Patient recently taken by ambulance to a city hospital because of unstable angina. He was discharged on 70/30 form of insulin, taking 25 units of insulin before breakfast and 15 units before supper. His blood sugar 4 hours after breakfast was 106. Insulin prescription was reduced daily. |
| 07/11/92 | No complaints from patient. All blood and urine tests are satisfactory. Insulin is now down to 8 units at breakfast, 0 units at lunch, and 3 units at supper. Spot blood sugar test was 148. |
| 07/20/92 | Patient down to zero insulin. All tests are negative. |

Some in the medical profession consider 40 u of insulin small and yet this amount can create an acceleration of the counter-regulatory response since it is more than needed. If urine test is neg, take 2 oz. of juice, if 1/10% take 1 oz.

| Date | Before bkft 7 am | 2 hrs. after bkft | before lunch 1 pm | 2 hrs. after lunch | before supper (6:30) | 2 hrs. after supper | Bed time | Insulin |
|---|---|---|---|---|---|---|---|---|
| 07/06/92 | | | | neg | neg | neg 8:30 | neg PM 147 | 25-0-10 |
| 07/07/92 | neg 117 | neg | neg | neg | neg | neg | neg | 20-0-7 |

-continued

| Date | Before bkft 7 am | 2 hrs. after bkft | before lunch 1 pm | 2 hrs. after lunch | before supper (6:30) | 2 hrs. after supper | Bed time | Insulin |
|---|---|---|---|---|---|---|---|---|
| 07/08/92 | neg 110 | neg | neg | neg | neg | neg | neg | 15-0-5 |
| 07/09/92 | neg 135 | neg | neg | neg | neg | neg | neg | 12-4 |
| 07/10/92 | neg 110 | neg | neg | neg | neg | neg | neg | 10-3 |
| 07/11/92 | neg | neg | neg 149 | neg | neg | neg 170 | neg | 8-3 |
| 07/12/92 | neg | neg | neg | neg 230 | neg | neg | neg 249 | 7-3 |
| 07/13/92 | neg 141 | neg | neg | neg 102 in my office | neg | neg | neg | 7 am 7-3 |
| 07/14/92 | neg | neg | neg | neg | neg | neg | neg | 7 am 7-2 |
| 07/15/92 | neg | neg | neg | neg | neg | neg | neg | 7 am 6-2 |
| 07/16/92 | neg | neg | neg | neg | neg | neg | neg | 7 am 5- |
| 07/17/92 | neg | neg | neg | neg | neg | neg | neg | 7 am 4-1 |
| 07/18/92 | neg | neg | neg | neg | neg | neg | neg | — |
| 07/19/92 | neg | neg | neg | neg | neg | neg | neg | 7 am 3– |
| 07/20/92 | neg | neg | neg | | | | | 9 am 2– |

EXAMPLE 2

Patient is 25 years of age.

| | |
|---|---|
| 09/16/91 | Patient complained of excessive thirst and urination of 2 months duration. Patient also was tired and drowsy causing him to have a car accident. Wt 165 Ht 5'5" Urine 2% sugar. Blood sugar 5½ hours after breakfast 270. Started on insulin. |
| 09/26/91 | Insulin is down from a peak of 31 units to present 12 units. Urine 1/10%. Blood sugar is 103, 6 hours after breakfast. |
| 10/05/91 | Wt 162½. Blood sugar 2 hours after breakfast is 116 on 3 units of regular insulin. Insulin to be reduced to 2 units for 4 days and then to be discontinued. |

It took 3 weeks to treat this young patient from start to finish. In the following Table, R is regular insulin, G is a glucose test and K is a ketones test.

| Date | Time | Test/Medication | Result/Dosage | Comment |
|---|---|---|---|---|
| 09/18/91 | 6:00 | Blood Glucose | 214 | Breakfast 6:30am |
| | 12:20 pm | Urine Glucose | 1000 | |
| | 12:20 pm | Urine Ketones | Negative | |
| | 12:20 pm | Blood Glucose | 220 | Lunch at 12:30 pm |
| | 2:20 pm | Urine Glucose | 1000 | |
| | 2:20 pm | Urine Ketones | Negative | |
| | 7:50 pm | Urine Glucose | 1000 | |
| | 7:50 pm | Urine Ketones | Negative | Dinner 8:00 pm |
| | 11:00 pm | Blood Glucose | 172 | |
| | 11:00 pm | Urine Glucose | Negative | |
| | 11:00 pm | Urine Ketones | Negative | Bed at 11:30 pm |
| 09/19/91 | 5:50 am | Blood Glucose | 178 | |
| | 5:50 am | Urine Glucose | Negative | |
| | 5:50 am | Urine Ketones | Negative | Breakfast 7:00 am |
| | 9:10 am | Urine Glucose | Negative | |
| | 9:10 am | Urine Ketones | Negative | |
| | 12:05 pm | Blood Glucose | 154 | |
| | 12:05 pm | Urine Glucose | Negative | |
| | 12:05 pm | Urine Ketones | Negative | Lunch 12:30 pm |
| | 2:50 pm | Urine Glucose | 500 | |
| | 2:50 pm | Urine Ketones | Negative | |
| | 8:35 pm | Insulin administered by Dr. Shohet | 8 units R/8 units NPH | Dinner 9:00 pm |
| | 8:55 pm | Urine Glucose | 100 | |
| | 8:55 pm | Urine Ketones | Negative | |
| | 11:05 pm | Blood Glucose | 89 | |
| | 11:05 pm | Urine Glucose | Negative | 3 oz. juice |
| | 11:05 pm | Urine Ketones | Negative | Bed at 11:30 pm |
| 09/20/91 | 5:40 am | Blood Glucose | 89 | |
| | 5:40 am | Urine Glucose | Negative | |
| | 5:40 am | Urine Ketones | Negative | |
| | 6:10 am | Insulin | 8 units R/8 units NPH | Breakfast 6:40 am |
| | 8:40 am | Urine Glucose | Negative | |
| | 8:40 am | Urine Ketones | Negative | 3 oz. juice |

-continued

| Date | Time | Test/Medication | Result/Dosage | Comment |
|---|---|---|---|---|
| | 12:30 pm | Urine Glucose | Negative | Lunch at 12:45 pm |
| | 12:30 pm | Urine Ketones | Negative | |
| | 12:30 pm | Insulin | 5 units R | Lunch at 12:45 pm |
| | 3:00 pm | Blood Glucose | 87 | |
| | 3:00 pm | Urine Glucose | Negative | |
| | 3:00 pm | Urine Ketones | Negative | 3 oz. juice |
| | 8:30 pm | Urine Glucose | Negative | |
| | 8:30 pm | Urine Ketones | 15 | |
| | 8:30 pm | Insulin | 5 units R/5 units NPH | Dinner at 9:00 pm |
| | 11:00 pm | Urine Glucose | 250 | 1 oz. juice |
| | 11:00 pm | Urine Ketones | Negative | |
| 09/21/91 | 1:30 am | Urine Ketones | Negative | |
| | 1:30 am | Urine Ketones | Negative | 3 oz. juice |
| | 1:30 am | Blood Glucose | 75 | Bed |
| | 8:15 am | Blood Glucose | 118 | |
| | 8:15 am | Urine Glucose | Negative | |
| | 8:15 am | Urine Ketones | Negative | |
| | 8:20 am | Insulin | 6 units R/6 units NPH | Breakfast at 8:40 am |
| | 11:00 am | Urine Glucose | 100 | 1 oz. juice |
| | 11:00 am | Urine Ketones | Negative | |
| | 12:40 pm | Urine Glucose | Negative | |
| | 12:40 pm | Urine Ketones | Negative | |
| | 12:50 pm | Blood Glucose | 64 | |
| | 1:00 pm | Insulin | 3 units R | Lunch at 1:00 pm |
| | 2:45 pm | Urine Glucose | Negative | |
| | 2:45 pm | Urine Ketones | Negative | 3 oz. juice |
| | 6:00 pm | Urine Glucose | Negative | |
| | 6:00 pm | Urine Ketones | Negative | |
| | 6:00 pm | Insulin | 4 units R/4 units NPH | Dinner at 6:30 pm |
| 09/22/91 | 2:30 am | Blood Glucose | 146 | |
| | 2:30 am | Urine Glucose | Negative | 2 oz. juice |
| | 2:30 am | Urine Ketones | Negative | |
| | 10:20 am | Urine Glucose | Negative | |
| | 10:20 am | Urine Ketones | Negative | |
| | 10:20 am | Blood Glucose | 108 | |
| | 10:30 am | Insulin | 5 units R/5 units NPH | Breakfast at 11:00 am |
| | 1:30 pm | Urine Glucose | 1000 | |
| | 1:30 pm | Urine Ketones | Negative | |
| | 1:30 pm | Blood Glucose | 186 | |
| | 3:00 pm | Urine Glucose | Negative | |
| | 3:00 pm | Urine Ketones | Negative | |
| | 3:00 pm | Insulin | 2 units R | Lunch at 3:30 pm |
| | 5:45 pm | Blood Glucose | 131 | |
| | 5:45 pm | Urine Glucose | Negative | |
| | 5:45 pm | Urine Ketones | Negative | 2 oz. juice |
| | 9:40 pm | Urine Glucose | Negative | |
| | 9:40 pm | Urine Ketones | Negative | |
| | 9:40 pm | Blood Glucose | 110 | |
| | 9:40 pm | Insulin | 4 units R/3 units NPH | Dinner at 9:50 pm |
| | 11:40 pm | Urine Glucose | Negative | |
| | 11:40 pm | Urine Ketones | Negative | 2 oz. juice/Bed |
| 09/23/91 | 6:15 am | Blood Glucose | 105 | |
| | 6:15 am | Urine Ketones | Negative | |
| | 6:15 am | Urine Glucose | Negative | |
| | 6:15 am | Insulin | 5 units R/4 units NPH | Breakfast at 6:45 am |
| | 9:15 am | Urine Ketones | Negative | |
| | 9:15 am | Urine Glucose | Negative | 2 oz. juice |
| | 11:50 am | Urine Ketones | Negative | |
| | 11:50 am | Urine Glucose | Negative | Lunch at 12:00 noon |
| | 2:10 pm | Urine G/K | 100/Negative | 1 oz. juice |
| | 7:20 pm | Blood Glucose | 158 | |
| | 7:20 pm | Urine G/K | Negative/Negative | |
| | 7:00 pm | Insulin | 2 units R/3 units NPH | Dinner at 7:45 pm |
| | 10:15 pm | Urine G/K | Negative/Negative | 2 oz. juice |
| | 10:15 pm | Blood Glucose | 117 | |
| 09/24/91 | 6:00 am | Urine G/K | Negative/Negative | |
| | 6:00 am | Blood Glucose | 116 | |
| | 6:1-5 am | Insulin | 4 units R/3 units NPH | Breakfast at 6:45 am |
| | 9:15 am | Urine G/K | 500/Negative | |
| | 10:25 am | Blood Glucose | 137 | |
| | 12:00 n | Urine G/K | Negative/Negative | Lunch at 12:30 pm |
| | 2:30 pm | Urine G/K | 1000/Negative | |
| | 7:10 pm | Urine G/K | 100/Negative | |
| | 7:10 pm | Blood Glucose | 142 | |
| | 7:15 pm | Insulin | 2 units R/3 units NPH | Dinner at 7:30 pm |
| | 9:30 pm | Urine G/K | Negative/Negative | 1 oz. juice |
| | 9:30 pm | Blood Glucose | 250 | |
| | 11:20 pm | Urine G/K | 500/Negative | |
| 09/25/91 | 6:15 am | Urine G/K | Negative/Negative | |
| | 6:20 am | Blood Glucose | 186 | |
| | 6:30 am | Insulin | 4 units R/3 units NPH | Breakfast at 7:00 am |

-continued

| Date | Time | Test/Medication | Result/Dosage | Comment |
|---|---|---|---|---|
| | 9:15 am | Urine G/K | 500/Negative | |
| | 11:45 am | Blood Glucose | 89 | |
| | 12:00 n | Urine G/K | N/N | Lunch at 12:15 pm |
| | 2:30 pm | Urine G/K | 1000/Negative | |
| | 2:30 pm | Blood Glucose | 248 | |
| | 7:40 pm | Blood Glucose | m | |
| | 7:40 pm | Urine G/K | N/N | |
| | 7:45 pm | Insulin | 2 units R/3 units NPH | Dinner at 8:00 pm |
| | 10:20 pm | Urine G/K | N/N | 2 oz. juice |
| 09/26/91 | 6:20 am | Urine G/K | N/N | |
| | 6:20 am | Blood Glucose | 144 | |
| | 6:25 am | Insulin | 4 units R/3 units NPH | Breakfast at 6:30 am |
| | 9:10 am | Urine G/K | N/N | 2 oz. juice |
| | 12:00 n | Blood Glucose | 84 | |
| | 12:10 pm | Urine G/K | N/N | Lunch at 12:15 pm |
| | 2:15 pm | Urine G/K | 500/Negative | |
| | 8:00 pm | Urine G/K | N/N | |
| | 8:00 pm | Insulin | 2 units R/2 units N | Dinner at 8:15 pm |
| | 10:30 pm | Urine G/K | N/N | Bed at 10:45 pm |
| 09/27/91 | 8:30 am | Urine G/K | Negative/15 | |
| | 8:40 am | Insulin | 4 units R/3 units N | |
| | 11:30 am | Urine G/K | 2000/Negative | |
| | 11:30 am | Blood Glucose | 199 | |
| | 12:45 pm | Urine G/K | 500/Negative | Lunch at 1:00 pm |
| | 3:00 pm | Urine G/K | Negative/Negative | 1 oz. juice |
| | 5:10 pm | Urine G/K | Negative/Negative | 1 oz. juice |
| | 8:30 pm | Urine G/K | Negative/Negative | |
| | 8:30 pm | insulin | 2 units R | Dinner at 9:00 pm |
| 09/28/91 | 1:30 am | Urine G/K | Negative/Negative | 1 oz. juice |
| | 8:50 am | Urine G/K | Negative/Negative | |
| | 8:50 am | Blood Glucose | 108 | |
| | 9:20 am | Insulin | 5 units R/2 units NPH | Breakfast at 9:45 am |
| | 11:50 am | Urine G/K | Negative/Negative | 1 oz. juice |
| | 2:30 pm | Urine G/K | Negative/Negative | Lunch at 3:00 pm |
| | 6:00 pm | Urine G/K | Negative/Negative | 6:00 pm 1 oz. juice |
| | 10:30 pm | Urine G/K | Negative/Negative | |
| | 10:30 pm | Insulin | 2 units R | Dinner at 10:45 pm |
| 09/29/91 | 2:50 am | Urine Glucose | Negative/Negative | 1 oz. juice |
| | 2:50 am | Blood Glucose | 104 | Bed |
| | 11:25 am | Blood Glucose | 143 | |
| | 11:25 am | Urine G/K | Negative/Negative | |
| | 11:25 am | Insulin | 5 units R | Breakfast at 11:55 am |
| | 2:30 pm | Urine G/K | 500/Negative | |
| | 4:45 pm | Urine G/K | Negative/Negative | 1 oz. juice |
| | 4:45 pm | Blood Glucose | 92 | Lunch |
| | 7:15 pm | Urine G/K | Negative/Negative | |
| | 7:15 pm | Insuhn | 2 units R | Dinner |
| | 9:30 am | Urine G/K | Negative/Negative | Bed at 10:00 pm |
| 09/30/91 | 5:35 am | Urine G/K | Negative/Negative | |
| | 5:35 am | Blood Glucose | 133 | |
| | 5:45 am | Insulin | 5 units R | Breakfast at 6:15 am |
| | 8:15 am | Blood Glucose | Negative/Negative | 1 oz. juice |
| | 12:15 pm | Urine G/K | Negative/Negative | Lunch at 12:30 pm |
| | 2:30 pm | Urine G/K | Negative/Negative | |
| | 8:30 pm | Urine G/K | Negative/Negative | Dinner at 9:00 pm |
| | 10:30 pm | Urine G/K | Negative/Negative | |
| | 10:30 pm | Blood Glucose | 131 | Bed at 11:00 pm |
| 10/01/91 | 5:45 am | Urine G/K | Negative/Negative | |
| | 5:45 am | Blood Glucose | 15 | |
| | 5:45 am | Insulin | 4 units R | Breakfast 6:15 am |
| | 8:15 am | Urine G/K | Negative/Negative | 1 oz. juice |
| | 12:00 n | Urine G/K | Negative/Negative | Lunch at 12:30 pm |
| | 2:30 am | Urine G/K | Negative/Negative | |
| | 8:15 pm | Urine G/K | Negative/Negative | Dinner at 9:15 pm |
| | 11:15 pm | Urine G/K | Negative/Negative | |
| | 11:15 pm | Blood Glucose | 129 | Bed at 11:30 pm |
| 10/02/91 | 5:45 am | Urine G/K | Negative/Negative | |
| | 5:45 am | Blood Glucose | 145 | |
| | 6:00 am | Insulin | 4 units R | Breakfast at 6:30 am |
| | 8:30 am | Urine G/K | Negative/Negative | 1 oz. juice |
| | 8:30 am | Blood Glucose | 119 | |
| | 11:30 am | Urine G/K | Negative/Negative | Lunch at 12:00 noon |
| | 2:00 pm | Urine G/K | 250/Negative | |
| | 8:30 pm | Urine G/K | Negative/Negative | Dinner at 9:00 pm |
| | 10:30 pm | Urine G/K | Negative/Negative | |
| | 10:30 pm | Blood Glucose | 134 | |
| 10/03/91 | 5:45 am | Urine G/K | Negative/Negative | |
| | 5:45 am | Blood Glucose | 140 | |
| | 5:45 am | Insuhn | 3 units R | Breakfast at 6:15 am |
| | 8:30 am | Urine G/K | 100/Negative | |
| | 11:35 am | Urine G/K | Negative/Negative | Lunch at 12:00 noon |

-continued

| Date | Time | Test/Medication | Result/Dosage | Comment |
|------|------|-----------------|---------------|---------|
|  | 2:00 pm | Urine G/K | Negative/Negative |  |
|  | 9:15 pm | Urine G/K | Negative/Negative |  |
|  | 11:15 pm | Urine | Negative/Negative |  |
|  | 11:15 pm | Blood Glucose | 121 |  |
| 10/04/91 | 6:30 am | Urine G/K | Negative/Negative |  |
|  | 6:30 am | Blood Glucose | 133 |  |
|  | 6:30 am | Insulin | 3 units R | Breakfast at 6:45 am |
|  | 9:00 am | Urine G/K | Negative/Negative | 1 oz. juice |
|  | 12:00 n | Urine G/K | Negative/Negative | Lunch |
|  | 2:00 pm | Urine G/K | Negative/Negative |  |
|  | 9:15 pm | Urine G/K | Negative/Negative |  |
|  | 9:15 pm | Blood Glucose | 62 | Dinner at 9:30 pm |
|  | 11:30 pm | Urine G/K | Negative/Negative |  |
| 10/05/91 | 7:20 am | Urine G/K | Negative/Negative |  |
|  | 7:20 am | Blood Glucose | 157 |  |
|  | 7:20 am | Insulin | 3 units R | Breakfast at 7:35 am |
|  | 9:45 am | Blood Glucose | 142 |  |
|  | 9:45 am | Urine G | Negative |  |
|  | 12:00 n | Urine G | Negative | 3-0-0 Lunch |

EXAMPLE 3

| | |
|---|---|
| 12/07/91 | Patient has a blood sugar level of 326 (normal blood sugar levels are up to 115, acceptable are up to 140, fair are less than 180). Patient has been a diabetic since 1986. Urine test reveals 4 + sugar and no albumin. Patient's vision is 20/20 with glasses. Patient has an abnormal EKG and rapid heart rate and feels terrible. He tried insulin and pills before without help. He felt bad with ups and downs on insulin some years earlier and decided not to take anything until now because he now felt ill. Patient was started on insulin as follows:<br>12 u NPH + 10 u regular before breakfast,<br>5 units regular before lunch, and<br>7 u NPH + 7 u regular before supper. |
| 12/14/91 | All tests are high. Patient is now on<br>19 u NPH + 19 u regular before breakfast,<br>13 units regular before lunch, and<br>20 u NPH + 19 u regular before supper.<br>Patient experienced less thirst and urination and felt stronger. Patients's blood pressure is still high. Wt. 243 - Blood sugar level is 205, 5 hours after lunch. |
| 12/21/91 | All tests are high. (on the dipstick it is difficult to tell the difference between 1 and 2% sugar. All the other colors [neg, 1/10%, 4% and ½ %] are easily distinguishable.) |
| 12/28/91 | Now on insulin as follows:<br>33 u NPH + 33 u regular at breakfast,<br>25 units regular at lunch, and<br>33 u NPH + 22 u regular at supper.<br>Patient's blood pressure is now normal, and his blood sugar is 352 (2½ hours after supper). EKG improved. All tests are high. |
| 01/04/92 | Patient is now on 46 u NPH + 46 u regular at breakfast, 37 units regular at lunch, and 43 u NPH + 45 u regular at supper. Wt 256½ (gained 13½ lbs.) Juice was to be given from 0-½% sugar in urine. |
| 01/11/92 | Patient showing ½% sugar in urine at times, 4% sugar in urine this morning. His blood sugar level 1 hour after supper is 170 (near normal for 1 hour after a meal). Patient now on insulin at 45 u NPH + 45 u regular at breakfast, 36 units regular at lunch and 42 u NPH + 44 u regular at supper. |
| 01/18/92 | Urine test is negative before breakfast for last 3 days, otherwise ¼-½%. Patient's blood sugar level 2½ hours after supper was 176. His urine sugar now is negative and juice was given to him here in the office (8 oz.). Patient is on insulin at 43 u NPH + 43 u regular ar breakfast, 34 units regular at lunch, and 40 u NPH + 42 u regular at supper. |
| 01/25/92 | Patient is now on insulin at 30 u NPH + 30 u regular at breakfast, 24 u regular at lunch, and 30 u NPH + 32 u regular at supper. Wt. 266½ lbs (gained an additional 10 lbs). His blood sugar 2 hours after supper was 195. His urine sugar was 4%. |
| 02/01/92 | Patient now on insulin at 26 u NPH + 26 u regular at breakfast, 16 units regular at lunch, and 27 u NPH + 29 u regular at supper, a drop of nearly 100 units from its peak. Patient failed to come back after this visit. He said he felt better than he had in years. |

This was a very instructive case. The patient had been a diabetic since 1986, not a new case. He tried insulin treatments in the past, with ups and downs including severe hypoglycemia. The effects were so bad, he had to give up the previous insulin treatments. Additionally, he was in terrible shape when he began this insulin plus sugar treatment. When he stopped coming, he was feeling well despite the fact that he was still on a large dose of insulin.

It took, over a month of daily increases in insulin dosages to reach this patient's peak requirement. However, the patient never once had an insulin reaction. He was beginning to have some negative urine tests in the morning, a most favorable sign. The applicant knew that the patient was reaching the peak of his insulin requirement while his urine sugars were still all 1-2% by the fact that the urine volume because much smaller, which meant that the total amount of sugar spilled in the urine was much smaller. It is believed that the patient was showing about 5% sugar in the urine at the onset and a 24 hour urine volume of nearly 4000 ccs. This means that he was spilling 40×5=200 grams of sugar/day. When his urine volume dropped to 1500 ccs/day and 2%-½% sugar range, it meant that he was now spilling 2×15=30 grams of sugar/day at most. And when he was showing ½% results (maximum), he was spilling only 7½ grams of sugar/day. No wonder he gained 25 pounds in the process. Still, his EKG improved and his blood pressure was normalized.

There was a good possibility that the patient's insulin requirements could have gone down to near zero if the present method was continued, especially if he had attempted to lose the weight that he had gained. The patient's test results are as follows:

12/08/91

| | | | | |
|---|---|---|---|---|
| Urine Test | 2% - 7 am | | Urine | 1% - 12:30 pm |
| Insulin - N.R. | 8 am | | Insulin | R11 - 1:00 pm |
| Breakfast | 8:30 am | | Lunch | 1:30 pm |
| Urine Test | 2% - 10 am | | Urine | 1% - 3:30 pm |
| Urine Test | 2% - 12 noon | | Urine | 1% - 5:30 pm |
| Insulin | 12 noon | | Insulin | N.R. 18-17 |
| Lunch | | | | 6 pm |
| Urine Test | 2% | | Dinner | 6:30 pm |
| Urine Test | 2% | | Urine | 1% - 8:30 pm |
| Insulin | N.R. | | Urine | 1% - 10:30 pm |
| Dinner | | | 12/13/91 | |
| Urine | 2% | | Urine | 1% - 7 am |
| Urine | 2% | | Insulin | N.R. - 19-19 |
| 12/09/91 | | | | 8 am |
| Urine | 2% - 7 am | | Breakfast | 8:30 am |
| Insulin | N.R. 11-11 | | Urine | 1% - 10:30 am |
| | 8 am | | Urine | 1% - 11:30 am |
| Breakfast | 8:30 am | | Insulin | R13 - 12 noon |
| Urine | 2% - 10 am | | Lunch | 12:30 pm |
| Urine | 2% - 12 noon | | Urine | 1% - 2:30 pm |
| Insulin R5 | 12:30 pm | | Urine | 1% - 4:30 pm |
| Lunch | 1 pm | | Insulin | N.R. 20-19 |
| Urine | 2% - 3 pm | | | 5:30 pm |
| Urine | 2% - 5 pm | | Dinner | 6 pm |
| Insulin | N.R. - 12-11 | | Urine | 1% - 8 pm |
| | 6 pm | | Urine | 1% - 10 pm |
| Dinner | 6:30 pm | | 12/14/91 | |
| Urine | 2% - 8:30 pm | | Urine | 1% - 7 am |
| Urine | 2% - 10:30 pm | | Insulin | N.R. 21-21 |
| 12/10/91 | | | | 8:30 am |
| Urine | 2% - 7 am | | Breakfast | 9 am |
| Insulin | N.R. 13-13 | | Urine | 2% - 11 am |
| | 8 am | | Urine | 2% - 12:30 pm |
| Breakfast | 8:30 am | | Insulin | 1 pm |
| Urine | 2% - 10:30 am | | Lunch | |
| Urine | 2% - 12:30 pm | | Urine | 2% - 3 pm |
| Insulin | R7 - 12:30 pm | | Urine | 2% - 5 pm |
| Lunch | 1 pm | | Insulin | 6 pm |
| Urine | 1% - 3 pm | | Dinner | 6:30 pm |
| Urine | 1% - 5 pm | | Urine | 2% - 8:30 pm |
| Insulin | N.R. 14-13 | | Urine | 2% - 11 pm |
| | 5:30 pm | | 12/15/91 | |
| Dinner | 6 pm | | Urine | 2% - 7 am |
| Urine | 11% - 8 pm | | Insulin | 8 am |
| Urine | 11% - 10 pm | | Breakfast | 8:30 am |
| 12/11/91 | | | Urine | 2% - 10:30 am |
| Urine | | | Urine | 2% - 12:30 pm |
| Insulin | N.R. 19-19 | | Insulin | 1 pm |
| Breakfast | | | Lunch | 1:30 pm |
| Urine | | | Urine | 2% - 3:30 pm |
| Urine | | | Urine | 2% - 5:30 pm |
| Insulin | R13 | | Insulin | 6 pm |
| Lunch | | | Dinner | 6:30 pm |
| Urine | | | Urine | 2% - 8:30 pm |
| Urine | | | Urine | 2% - 10:30 pm |
| Insulin | N.R. 20-19 | | 12/16/91 | |
| Dinner | | | Urine | 2% - 7 am |
| Urine | | | Insulin | N.R. 21-21 |
| Urine | | | | 8 am |
| 12/11/91 | | | Breakfast | 8:30 am |
| Urine | 1% - 7 am | | Urine | 2% - 10:30 am |
| Insulin | N.R. 15-15 | | Urine | 2% - 12:30 pm |
| | 8 am | | Insulin | R15 - 1 pm |
| Breakfast | 8:30 am | | Lunch | 1:30 pm |
| Urine | 1% - 10 am | | Urine | 2% - 3:30 pm |
| Urine | 1% - 12 noon | | Urine | 2% - 5:30 pm |
| Insulin | R9 - 12:30 pm | | Insulin | N.R. 22-21 |
| Lunch | 1 pm | | | 6 pm |
| Urine | 1% - 3 pm | | Dinner | 6:30 pm |
| Urine | 1% - 5 pm | | Urine | 2% - 8:30 pm |
| Insulin | N.R. 16-15 | | Urine | 2% - 10:30 pm |
| | 6 pm | | 12/17/91 | |
| Dinner | 6:30 pm | | Urine | 7 am |
| Urine | 1% - 8:30 pm | | Insulin | N.R. 22-22 |
| Urine | 1% - 10:30 pm | | | 8 am |
| 12/12/91 | | | Breakfast | 8:30 am |
| Urine | 1% - 7 am | | Urine | 10:30 am |
| Insulin | N.R. 17-17 | | Urine | 12:30 pm |
| | 8 am | | Insulin | R16 - 1 pm |
| Breakfast | 8:30 am | | Lunch | 1:30 pm |
| Urine | 1% - 10:30 am | | Urine | 3:30 pm |

| | | | | |
|---|---|---|---|---|
| Urine | 5:30 pm | | Insulin | N.R. 28-27 |
| Insulin | N.R. 23-22 | | | 6:30 pm |
| | 6 pm | | Dinner | 7 pm |
| Dinner | 6:30 pm | | Urine | 2% - 9 pm |
| Urine | 8:30 pm | | Urine | 2% - 11 pm |
| Urine | 10:30 pm | | 12/23/91 | |
| 12/18/91 | | | Urine | 7 am |
| Urine | 2% - 7 am | | Insulin | N.R. 28-28 |
| Insulin | N.R. 23-23 | | | 8 am |
| | 8 am | | Breakfast | 8:30 am |
| Breakfast | 8:30 am | | Urine | 2% - 10:30 am |
| Urine | 2% - 10:30 am | | Urine | 2% - 12:30 pm |
| Urine | 2% - 12:30 pm | | Insulin | R21 - 1 pm |
| Insulin | R17 - 1 pm | | Lunch | 1:30 pm |
| Lunch | 1:30 pm | | Urine | 2% - 3:30 pm |
| Urine | 2% - 3:30 pm | | Urine | 2% - 5:30 pm |
| Urine | 2% - 3:30 pm | | Insulin | N.R. 29-28 |
| Insulin | N.R. 24-23 | | | 6 pm |
| | 6 pm | | Dinner | 6:30 pm |
| Dinner | 6:30 pm | | Urine | 2% - 8:30 pm |
| Urine | 2% - 8:30 pm | | Urine | 2% - 10:30 pm |
| Urine | 2% - 8:30 pm | | 12/24/91 | |
| 12/19/91 | | | Urine | 2% - 7 am |
| Urine | 2% - 7 am | | Insulin | N.R. 29-29 |
| Insulin | N.R. 24-24 | | | 8 am |
| | 8 am | | Breakfast | 8:30 am |
| Breakfast | 8:30 am | | Urine | 2% - 10.30 am |
| Urine | 2% - 10:30 am | | Urine | 2% - 12:30 pm |
| Urine | 2% - 12:30 pm | | Insulin | R22 - 1 pm |
| Insulin | R18 - 1 pm | | Lunch | 1:30 pm |
| Lunch | 1:30 pm | | Urine | 2% - 3:30 pm |
| Urine | 2% - 3:30 pm | | Urine | 2% - 5:30 pm |
| Urine | 2% - 5:30 pm | | Insulin | N.R. 30-29 |
| Insulin | N.R. 25-24 | | | 6 pm |
| | 6 pm | | Dinner | 6:30 pm |
| Dinner | 6:30 pm | | Urine | 2% - 8:30 pm |
| Urine | 2% - 8:30 pm | | Urine | 2% - 10:30 pm |
| Urine | 2% - 10:30 pm | | 12/25/91 | |
| 12/20/91 | | | Urine | 2% - 7 am |
| Urine | 2% - 7 am | | Insulin | N.R. 30-30 |
| Insulin | N.R. 25-25 | | | 8 am |
| | 8 am | | Breakfast | 8:30 am |
| Breakfast | 8:30 am | | Urine | 2% - 10:30 am |
| Urine | 2% - 10:30 am | | Urine | 2% - 12:30 pm |
| Urine | 2% - 12:30 pm | | Insulin | R22 - 1 pm |
| Insulin | R19 - 1 pm | | Lunch | 1:30 pm |
| Lunch | 1:30 pm | | Urine | 2% - 3:30 pm |
| Urine | 2% - 3:30 pm | | Urine | 2% - 5:30 pm |
| Urine | 2% - 5:30 pm | | Insulin | N.R. 31-30 |
| Insulin | N.R. 26-25 | | | 6 pm |
| | 6 pm | | Dinner | 6:30 pm |
| Dinner | 6:30 pm | | Urine | 2% - 8:30 pm |
| Urine | 2% - 8:30 pm | | Urine | 2% - 10:30 pm |
| Urine | 2% - 10:30 pm | | 12/26/91 | |
| 12/21/91 | | | Urine | 2% - 7 am |
| Urine | 2% - 7 am | | Insulin | N.R. 31-31 |
| Insulin | N.R. 26-26 | | | 8 am |
| | 8:30 am | | Breakfast | 8:30 am |
| Breakfast | 9 am | | Urine | 2% - 10:30 am |
| Urine | 2% - 11 am | | Urine | 2% - 12:30 pm |
| Urine | 2% - 1 pm | | Insulin | R23 - 1 pm |
| Insulin | R20 - 2 pm | | Lunch | 1:30 pm |
| Lunch | 2:30 pm | | Urine | 2% - 3:30 pm |
| Urine | 2% - 4:30 pm | | Urine | 2% - 5:30 pm |
| Urine | 2% - 6:30 pm | | Insulin | N.R. 32-31 |
| Insulin | N.R. 27-26 | | | 6 pm |
| | 7 pm | | Dinner | 6:30 pm |
| Dinner | 7:30 pm | | Urine | 2% - 8:30 pm |
| Urine | 2% - 9:30 pm | | Urine | 2% - 10:30 pm |
| Urine | 2% - 11:30 pm | | 12/27/91 | |
| 12/22/91 | | | Urine | 2% - 7 am |
| Urine | 2% - 7 am | | Insulin | N.R. 32-32 |
| Insulin | N.R. 27-27 | | | 8 am |
| | 8:30 am | | Breakfast | 8:30 am |
| Breakfast | 9 am | | Urine | 2% - 10:30 am |
| Urine | 2% - 11 am | | Urine | 2% - 12:30 pm |
| Urine | 2% - 1 pm | | Insulin | R24 - 1 pm |
| Insulin | R21 - 1:30 pm | | Lunch | 1:30 pm |
| Lunch | 2 pm | | Urine | 2% - 3:30 pm |
| Urine | 2% - 4 pm | | rine | 2% - 5:30 pm |
| Urine | 2% - 6 pm | | Insulin | N.R. 33-32 |

-continued

| | | |
|---|---|---|
| | | 6 pm |
| Dinner | 6:30 pm | |
| Urine | 2% - 8:30 pm | |
| Urine | 2% - 10:30 pm | |
| _12/28/91_ | | |
| Urine | 2% - 8 am | |
| Insulin | N.R. 32-32 | |
| | 10 am | |
| Breakfast | 10:30 am | |
| Urine | 2% - 12:30 pm | |
| Urine | 2% - 2:30 pm | |
| Insulin | R24 - 3 pm | |
| Lunch | 3:30 pm | |
| Urine | 2% - 5:30 pm | |
| Urine | 2% - 7:30 pm | |
| Insulin | N.R. 33-32 | |
| | 8 pm | |
| Dinner | 8:30 pm | |
| Urine | 2% - 10:30 pm | |
| Urine | 2% - 12 midn | |
| _12/29/91_ | | |
| Urine | 2% - 8 am | |
| Insulin | N.R. 34-34 | |
| | 8:30 am | |
| Breakfast | 9 am | |
| Urine | 2% - 11 am | |
| Urine | 2% - 1 pm | |
| Insulin | R27 - 1 pm | |
| Lunch | 1:30 pm | |
| Urine | 2% - 3:30 pm | |
| Urine | 2% - 5:30 pm | |
| Insulin | N.R. 33-34 | |
| | 6 pm | |
| Dinner | 6:30 pm | |
| Urine | 2% - 8:30 pm | |
| Urine | 2% - 10:30 pm | |
| _12/30/91_ | | |
| Urine | 12% - 7 am | |
| Insulin | N.R. 36-36 | |
| | 8 am | |
| Breakfast | 8:30 am | |
| Urine | 2% - 10:30 am | |
| Urine | 2% - 12:30 pm | |
| Insulin | R29 - 1 pm | |
| Lunch | 1:30 pm | |
| Urine | 2% - 3:30 pm | |
| Urine | 2% - 5:30 pm | |
| Insulin | N.R. 35-36 | |
| | 6 pm | |
| Dinner | 6:30 pm | |
| Urine | 2% - 8:30 pm | |
| Urine | 2% - 10:30 pm | |
| _12/31/91_ | | |
| Urine | 2% - 7 am | |
| Insulin | N.R. 38-38 | |
| | 8 am | |
| Breakfast | 8:30 am | |
| Urine | 2% - 10:30 am | |
| Urine | 2% - 12:30 pm | |
| Insulin | R31 - 1 pm | |
| Lunch | 1:30 pm | |
| Urine | 2% - 3:30 pm | |
| Urine | 2% - 5:30 pm | |
| Insulin | N.R. 37-39 | |
| | 6 pm | |
| Dinner | 6:30 pm | |
| Urine | 2% - 8:30 pm | |
| Urine | 2% - 8:30 pm | |
| _01/01/92_ | | |
| Urine | 2% - 8:30 am | |
| Insulin | N.R. 40-40 | |
| | 9 am | |
| Breakfast | 9:30 am | |
| Urine | 2% - 11:30 am | |
| Urine | 2% - 1:30 pm | |
| Insulin | R33 - 2 pm | |
| Lunch | 2:30 pm | |
| Urine | 2% - 4:30 pm | |
| Urine | 2% - 6:30 pm | |
| Insulin | N.R. 39-41 | |
| | 7 pm | |

-continued

| | | |
|---|---|---|
| Dinner | 7:30 pm | |
| Urine | 2% - 9:30 pm | |
| Urine | 2% - 11 pm | |
| _01/02/92_ | | |
| Urine | 2% - 7 am | |
| Insulin | N.R. 42-42 | |
| | 8 am | |
| Breakfast | 8:30 am | |
| Urine | 2% - 10:30 am | |
| Urine | 2% - 12:30 pm | |
| Insulin | R35 - 1 pm | |
| Lunch | 1:30 pm | |
| Urine | 2% - 3:30 pm | |
| Urine | 2% - 5:30 pm | |
| Insulin | N.R. 41-43 | |
| | 6 pm | |
| Dinner | 6:30 pm | |
| Urine | 2% - 8:30 pm | |
| Urine | 2% - 10:30 pm | |
| _01/03/92_ | | |
| Urine | 2% - 7 am | |
| Insulin | N.R. 44-44 | |
| | 8 am | |
| Breakfast | 8:30 am | |
| Urine | 2% - 10:30 am | |
| Urine | 2% - 12:30 pm | |
| Insulin | R37 - 1 pm | |
| Lunch | 1:30 pm | |
| Urine | 2% - 3:30 pm | |
| Urine | 2% - 3:30 pm | |
| Insulin | N.R. 43-4 | |
| | 6 pm | |
| Dinner | 6:30 pm | |
| Urine | 2% - 8:30 pm | |
| Urine | 2% - 10:30 pm | |
| _01/04/92_ | | |
| Urine | 2% - 8 am | |
| Insulin | N.R. 46-46 | |
| | 10:30 am | |
| Breakfast | 11 am | |
| Urine | | |
| Urine | 2% - 12:30 pm | |
| Insulin | R35 - 2 pm | |
| Lunch | 2:30 pm | |
| Urine | 2% - 4:30 pm | |
| Urine | 2% - 6:30 pm | |
| Insulin | N.R. 47-48 | |
| | 7 pm | |
| Dinner | 7:30 pm | |
| Urine | 1% - 9:30 pm | |
| Urine | 1% - 11 pm | |
| _01/05/92_ | | |
| Urine | 1% - 8 am | |
| Insulin | N.R. 46-46 | |
| | 9 am | |
| Breakfast | 9:30 am | |
| Urine | 2% - 11:30 am | |
| Urine | 1% - 1:30 pm | |
| Insulin | R30 - 1:30 pm | |
| Lunch | 2 pm | |
| Urine | 2% - 4 pm | |
| Urine | 2% - 6 pm | |
| Insulin | N.R. 47-48 | |
| | 6 pm | |
| Dinner | 6:30 pm | |
| Urine | 1% - 8:30 pm | |
| Urine | 1% - 10:30 pm | |
| _01/06/92_ | | |
| Urine | 1% - 7 am | |
| Insulin | N.R. 46-46 | |
| | 8 am | |
| Breakfast | 8:30 am | |
| Urine | 1% - 10:30 am | |
| Urine | 1% - 12:30 pm | |
| Insulin | R30 - 1 pm | |
| Lunch | 1:30 pm | |
| Urine | 1% - 3:20 pm | |
| Urine | 1% - 5:30 pm | |
| Insulin | N.R. 47-48 | |
| | 6 pm | |
| Dinner | 6:30 pm | |

-continued

| | |
|---|---|
| Urine | ½% - 8:30 pm |
| Urine | 1% - 10:30 pm |
| 01/07/92 | |
| Urine | ½ - 7 am |
| Insulin | N.R. 46-46 |
| | 8 am |
| Breakfast | 8:30 am |
| Urine | 1% - 10:30 am |
| Urine | 1% - 12:30 pm |
| Insulin | R30 - 1 pm |
| Lunch | 1:30 pm |
| Urine | 1% - 3:30 pm |
| Urine | 1% - 5:30 pm |
| Insulin | N.R. 47-48 |
| | 6 pm |
| Dinner | 6:30 pm |
| Urine | 1% - 8:30 pm |
| Urine | 1½% - 10:30 pm |
| 01/08/92 | |
| Urine | ½% - 7 am |
| Insulin | N.R. 46-46 |
| | 8 am |
| Breakfast | 8:30 am |
| Urine | ½% - 10:30 am |
| Urine | 1% - 12:30 pm |
| Insulin | R30 - 1:30 pm |
| Lunch | 2 pm |
| Urine | ½% - 4 pm |
| Urine | 1% - 6 pm |
| Insulin | 6:30 pm |
| Dinner | 7 pm |
| Urine | 1% - 9 pm |
| Urine | 1% - 11 pm |
| 01/09/92 | |
| Urine | 1% - 7 am |
| Insulin | N.R. - 46-46 |
| | 8 am |
| Breakfast | 8:30 am |
| Urine | ½% - 10:30 am |
| Urine | ½% - 12:30 pm |
| Insulin | R30 - 1 pm |
| Lunch | 1:30 pm |
| Urine | ½% - 3:30 pm |
| Urine | ½% - 5:30 pm |
| Insulin | N.R. 47-48 |
| | 6 pm |
| Dinner | 6:30 pm |
| Urine | ½% - 8:30 pm |
| Urine | ½% - 10:30 pm |
| 01/10/92 | |
| Urine | ½% - 7 am |
| Insulin | N.R. 46-46 |
| | 8 am |
| Breakfast | 8:30 am |
| Urine | 1% - 10:30 am |
| Urine | 1% - 12:30 pm |
| Insulin | R30 - 1 pm |
| Lunch | 1:30 pm |
| Urine | ½% - 3:30 pm |
| Urine | ½% - 5:30 pm |
| Insulin | N.R. 47-48 |
| | 6 pm |
| Dinner | 6:30 pm |

-continued

| | |
|---|---|
| Urine | ½% - 8:30 pm |
| Urine | 1½% - 10:30 pm |
| 01/11/92 | |
| Urine | 4% - 8 am |
| Insulin | N.R. 45-45 |
| | 11 am |
| Breakfast | 11:30 am |
| Urine | ½% - 12:30 pm |
| Urine | ½% - 3 pm |
| Insulin | R36 - 3:30 pm |
| Lunch | 4 pm |
| Urine | ½% - 5:30 pm |
| Urine | ½% - 7:30 pm |
| Insulin | N.R. 42-44 |
| | 7:30 pm |
| Dinner | 8 pm |
| Urine | 1% - 10 pm |
| Urine | 1% - 11 |

EXAMPLE 4

This man suffered a heart attack on Apr. 14, 1992. He was hospitalized until Apr. 24, 1992. His blood sugars and insulins are listed below:

| | Blood Sugars | | | | Insulin | | |
|---|---|---|---|---|---|---|---|
| Date | 7 am | 11:30 am | 4:30 pm | 10 pm | B.B. N.R. | B.L. R | B.S. N.R. |
| 04/14/92 | | | 289 | 228 | | 6 | 4 |
| 04/15/92 | 295 | 256 | 202 | 173 | 9 + 9 | 5 | 7 + 7 |
| 04/16/92 | 218 | 208 | 324 | 276 | 10 + 10 | 6 | 7 + 7 |
| 04/17/92 | 183 | 142 | 136 | 159 | 8 + 9 | 5 | 8 + 8 |
| 04/18/92 | 168 | 149 | 105 | 102 | 7 + 8 | 4 | 7 + 7 |
| 04/19/92 | 135 | 103 | 91 | 123 | 6 + 7 | 3 | 6 + 6 |
| 04/20/92 | 138 | 146 | 226 | 100 | 5 + 6 | 3 | 6 + 6 |
| 04/21/92 | 120 | 121 | 98 | 102 | 4 + 5 | 2 | 5 + 5 |
| 04/22/92 | 153 | 168 | 68 | 145 | 3 + 5 | 1 | 4 + 4 |
| 04/23/92 | 112 | 103 | 111 | 125 | 3 + 4 | 0 | 3 + 3 |
| 04/24/92 | 91 | 111 | | | 3 + 3 | 0 | 3 + 3 |

As is clear from the above, when the patient's blood sugar dropped to 91 (a normal figure but low in the context of the prevailing blood sugars then), he flared up the next day. It happened again when he dropped to 98. However, on low insulin dosages on April 22, even a blood sugar level of 68 did not cause a flare up.

At home, while all tests were negative, the patient managed to gain 10 lbs. He was kept on 3 units for many days and then 2 units for many days and then 1 unit to remind him that he is still a diabetic, but compensated.

The patient's diet was more than the 1500 calories he believed he was taking (the patient gained weight). The patient also took snacks. As long as the patient followed the diet as described above, when the patient is not taking insulin, he can distribute his food any way he chooses.

Since his discharge from the hospital, the patient was seen on

| | |
|---|---|
| 05/01/92 | Wt. 172 BP normal Abnormal EKG - Spot check of blood sugar 138. All urines were negative. |
| 05/15/92 | Wt. 177 BP 12/70. Blood sugar 2 hours after lunch 104. Insulin 2R - 0 - 2R. EKG improved. |
| 05/23/92 | Blood sugar 135 - 1 hours after supper. Al urines were negative. |
| 06/16/92 | Blood sugar 140 - 1½ hrs after lunch (normal) |
| 07/09/92 | Wt. 182. Watts hours without symptoms. Blood sugar 3 hours after lunch 99. He was off the insulin. |

The patient was in Parkway Hospital from Apr. 14, 1992 to Apr. 24, 1992 and was discharged at 1:00 pm on Apr. 24, 1992. His regiment was as follows after his release:

1. 
    a) Medication for Friday, Apr. 24, 1992—dinner
       Insulin-3R units (Humulin) 3N units
       half hour by dinner
    b) 1 baby aspirin
    c) 1 oz. orange juice, two hours after dinner
    d) check urine for negative two hours after dinner
2. Dinner
   6:00 pm
   6 oz. chicken bouillon soup
   1 stuffed tomato with 4 oz. s.f. tuna mix
   1 slice diet whole wheat bread
   4 oz. S.F. broccoli
   4 oz. unsweetened applesauce
   6 oz. decaffeinated coffee
   Urinalysis
3. Check urine 1 hour after dinner—test negative
   Snack:
       raisins and s.f. nuts—2 oz.
       Avoid: sugar, chips, candy, pickles, soda, cold cuts (eat s.f. turkey), regular coffee, reg. hot dogs (eat chicken franks), chocolate, salt

| 04/25/92 |
| --- |
| Medication - ½ hr. before breakfast<br>   3 units of R - Humulin<br>   3 units of N - Humulin<br>b) 1 vasotec tablet - 5 mg daily<br>c) 1 oz. orange juice - 2 hrs. after breakfast<br>d) 1 baby aspirin<br>e) ½ hr. before dinner<br>   3 units of R - Humulin<br>   3 units of N - Humulin<br>f) 1 oz. orange juice 2 hrs. after dinner |

| Menu | | |
| --- | --- | --- |
| Breakfast | Lunch | Dinner |
| 4 oz. prune juice | 4 oz. beef s.f. soup | 4 oz. s.f. chicken soup |
| 6 oz. cooked oatmeal | 4 oz. s.f. cheese with crackers | 8 oz. baked chicken |
| 1 oz. s.f. cheese | 4 oz. green beans | 4 oz. s.f. broccoli |
| 2 cooked egg whites | 4 oz. jello, diet | 1 slice bread, whole wheat |
| 1 slice whole wheat bread | 4 oz. skim milk | 4 oz. diet peaches |
| 1 pat s.f. margarine | 6 oz. coffee, decaf | 4 oz. skim milk |
| 4 oz. unsweetened applesauce | | 6 oz. decaf coffee |
| 8 oz. decaf coffee 4 oz. skim milk | | |
| Snack: Raisins s.f. and 4 oz. nuts | Urine Test: 2 hrs. after breakfast - negative | |
| | 2 hrs. after dinner - negative | |

| 04/26/92 |
| --- |
| Medication - ½ hr. before breakfast<br>   3 units of R - Humulin<br>   3 units of N - Humulin<br>b) 1 vasotec tablet - 5 mg daily<br>c) 1 oz. orange juice - 2 hrs. after breakfast<br>d) 1 baby aspirin<br>e) ½ hr. before dinner<br>   3 units of R - Humulin<br>   3 units of N - Humulin<br>f) 1 oz. orange juice 2 hrs. after dinner |

| Menu | | |
| --- | --- | --- |
| Breakfast | Lunch | Dinner |
| 1 grapefruit | 4 oz. s.f. chicken bouillon soup | 4 oz. s.f beef bouillon soup |
| 2 egg whites | 4 oz. s.f. cheese | 4 oz. sliced turkey |
| 1 slice whole wheat toast | 2 oz. s.f. crackers | 4 seasoned rice |
| diet applesauce | 4 oz. green beans | 4 oz. green beans |
| decaf coffee | 4 oz. juice | 8 oz. skim milk |
| skim milk | 4 oz. skim milk | 4 oz. diet peaches |
| | 4 oz. diet jello | 6 oz. decaf coffee |
| Snack: 3 graham crackers | Urine Test: 2 hrs. after breakfast - negative | |
| 8 oz. skim milk | 2 hrs. after dinner - negative | |

| 04/27/92 |
| --- |
| Medication - ½ hr. before breakfast<br>   3 units of R - Humulin<br>   3 units of N - Humulin<br>b) 1 vasotec tablet - 5 mg daily<br>c) 1 oz. orange juice - 2 hrs. after breakfast<br>d) 1 baby aspirin<br>e) ½ hr. before dinner |

04/27/92

3 units of R - Humulin
1 unit of N - Humulin
f) 1 oz. orange juice 2 hrs. after dinner

Menu

| Breakfast | Lunch | Dinner |
|---|---|---|
| 1 grapefruit | s.f. chicken bouillon soup | s.f. beef bouillon soup |
| 2 oz. cooked oatmeal | 4 oz. diet tuna salad | 4 oz. sliced turkey |
| 2 pancakes | lettuce/tomato | 4 oz. broccoli |
| 2 oz. diet syrup | 4 oz. diet fruit | baked potato slices |
| 4 oz. diet applesauce | 8 oz. skim milk | diet jello |
| 6 oz. decaf coffee | 4 bz. spinach | skim milk |
| 8 oz. skim milk | | diet iced tea |

Snack: 4 oz. diet popcorn    Urine Test: 2 hrs. after breakfast - negative
                                         2 hrs. after dinner - negative

04/28/92

Medication - ½ hr. before breakfast
3 units of R - Humulin
1 unit of N - Humulin
b) 1 vasotec tablet - 5 mg daily
c) 1 oz. orange juice - 2 hrs. after breakfast
d) 1 baby aspirin
e) ½ hr. before dinner
3 units of R - Humulin
1 unit of N - Humulin
f) 1 oz. orange juice 2 hrs. after dinner

Menu

| Breakfast | Lunch | Dinner |
|---|---|---|
| 1 grapefruit | s.f. beef bouillon | s.f. chicken soup |
| 4 oz. cooked oatmeal | baked chicken | 1 baked pork chop |
| 2 french toast | 4 oz. green beans | 4 oz. broccoli |
| 2 oz. diet syrup | 4 oz. rice | 1 baked potato |
| 4 oz. diet fruit | 4 oz. diet jello | diet jello |
| 6 oz. decaf coffee | skim milk | skim milk |
| 8 oz. skim milk | | 4 oz. iced tea |

Snack: 3 graham crackers    Urine Test: 2 hrs. after breakfast - negative
       8 oz. skim milk                  2 hrs. after dinner - negative

04/29/92

Medication - ½ hr. before breakfast
3 units of R - Humulin
1 unit of N - Humulin
b) 1 vasotec tablet - 5 mg daily
c) 1 oz. orange juice - 2 hrs. after breakfast
d) 1 baby aspirin
e) ½ hr. before dinner
3 units of R - Humulin
1 unit of N - Humulin
f) 1 oz. orange juice 2 hrs. after dinner

Menu

| Breakfast | Lunch | Dinner |
|---|---|---|
| 1 grapefruit | s.f chicken bouillon | s.f. beef bouillon |
| cooked cereal | 4 oz. tuna fish | 4 oz. pork chop |
| 4 oz. salmon cakes | 4 oz. lettuce/tomatoes | 4 oz. applesauce |
| 4 oz. diet fruit | 2 oz. s.f. cheese | 4 oz. broccoli |
| 4 oz. skim milk | 2 oz. s.f. crackers | skim milk |
| 8 oz. coffee | skim milk | diet jello |
| | decaf coffee | |

Snack: 4 oz. diet popcorn    Urine Test: 2 hrs. after breakfast - negative
                                         2 hrs. after dinner - negative

04/30/92

Medication - ½ hr. before breakfast
3 units of R - Humulin
1 unit of N - Humulin
b) 1 vasotec tablet - 5 mg daily
c) 1 oz. orange juice - 2 hrs. after breakfast
d) 1 baby aspirin
e) ½ hr. before dinner
3 units of R - Humulin
1 unit of N - Humulin
f) 1 oz. orange juice 2 hrs. after dinner

Menu

| Breakfast | Lunch | Dinner |
|---|---|---|
| 1 grapefruit | s.f. beef bouillon | s.f. chicken bouillon |
| cooked cereal | 8 oz. baked chicken | 4 oz. baked ham |
| 2 pancakes | green beans | broccoli |
| 2 oz. diet syrup | diet jello | baked potato |
| 4 oz. skim milk | skim milk | skim milk |
| 8 oz. coffee | coffee | iced tea |
| diet fruit | 4 oz. sliced bread (2) | jello |
| | | fresh strawberries |

Snack: 4 oz. diet popcorn    Urine Test: 2 hrs. after breakfast - negative
                                         2 hrs. after dinner - negative

05/01/92

Medication - ½ hr. before breakfast
3 units of R - Humulin
1 unit of N - Humulin
b) 1 vasotec tablet - 5 mg daily
c) 1 oz. orange juice - 2 hrs. after breakfast
d) 1 baby aspirin
e) ½ hr. before dinner
3 units of R - Humulin
1 unit of N - Humulin
f) 1 oz. orange juice 2 hrs. after dinner
*STOP "N units" of Humulin as of today - 5/1/92

Menu

| Breakfast | Lunch | Dinner |
|---|---|---|
| 1 grapefruit | 4 oz. beef soup | 4 oz. s.f. chicken soup |
| 4 oz. s.f. cheese | 4 oz. salmon cakes | 8 oz. baked chicken |
| 2 oz. crackers | lettuce/tomato | 4 oz. broccoli |
| cooked cereal | cooked cabbage | 4 oz. sweet potatoes |
| skim milk | 4 oz. diet fruit | 4 oz. diet jello |
| diet fruit | 8 oz. skim milk | 8 oz. diet tea |
| 8 oz. decaf coffee | 8 oz. hot tea | |

Snack: diet popcorn    Urine Test: 2 hrs. after breakfast - negative
                                   2 hrs. after dinner - negative

05/02/92

Medication - 1 baby aspirin - daily
b) 1 vasotec - 5 mg daily
c) 3 units R - Humulin - daily
   ½ hr. before breakfast                # of calories daily?
d) 1 oz. orange juice - 2 hrs. after breakfast

05/02/92 e) 3 units - R - Humulin - ½ hr. before dinner  
    f) 1 oz. orange juice 2 hrs. after dinner

Menu

| Breakfast | Lunch | Dinner |
|---|---|---|
| 1 grapefruit | 4 oz. beef soup | 4 oz. chicken soup |
| 4 oz. cooked cereal | 4 oz. pork chop | 4 oz. tuna salad |
| 2 pancakes | 4 oz. green beans | w/1 tomato/lettuce |
| 2 oz. diet syrup | 4 crackers | 6 crackers |
| 4 oz. unsweetened applesauce | 4 oz. jello | jello |
| 8 oz. skim milk | skim milk | 8 oz. decaf coffee |
| | 8 oz. decaf coffee | |

Snack: 3 graham crackers  
        8 oz. skim milk

Urine Test: 2 hrs. after breakfast - negative  
            2 hrs. after dinner - negative

05/03/92

Medication - ½ hr. before breakfast  
    3 units R - Humulin  
    b) 1 vasotec - 0.5 mg daily  
    c) 1 oz. orange juice - 2 hrs. after breakfast  
    d) 1 baby aspirin  
    e) 3 units - R - Humulin - ½ hr. before dinner  
    f) 1 oz. orange juice 2 hrs. after dinner

Menu

| Breakfast | Lunch | Dinner |
|---|---|---|
| 1 grapefruit | 4 oz. chicken soup | 4 oz. s.f. chicken soup |
| 4 oz. cooked cereal | 8 oz. baked chicken | 8 oz. chicken |
| 4 oz. s.f. cheese | 4 oz. sweet potatoes | 4 oz. steamed cabbage |
| 4 crackers | 4 oz. lettuce and tomato | 4 oz. oven fried potatoes |
| 4 oz. diet peaches | 4 oz. jello | 4 oz. jello |
| 8 oz. skim milk | 4 oz. skim milk | 8 oz. diet iced tea |
| 8 oz. decaf coffee | | |

Snack: 4 oz. s.f. popcorn  
Urine Test: 2 hrs. after breakfast - negative  
            2 hrs. after dinner - negative

05/04/92

Medication - ½ hr. before breakfast  
    3 units R - Humulin  
    b) 1 vasotec - 0.5 mg daily  
    c) 1 oz. orange juice - 2 hrs. after breakfast  
    d) 1 baby aspirin  
    e) 3 units - R - Humulin - ½ hr. before dinner  
    f) 1 oz. orange juice 2 hrs. after dinner

Menu

| Breakfast | Lunch | Dinner |
|---|---|---|
| 1 grapefruit | 4 oz. beef soup | 8 oz. s.f. chicken soup |
| 4 oz. cooked cereal | 4 oz. s.f. cheese | 8 oz. baked chicken |
| 2 pancakes | 2 slices whole wheat bread | 4 oz. steamed cabbage |
| 2 oz. syrup | 2 oz. tuna mix | 4 oz. s.f. rice |
| 8 oz. skim milk | 4 oz. diet peaches | 4 oz. diet peaches |
| 8 oz. decaf coffee | 4 oz. skim milk | 1 slice whole wheat bread |
| | 8 oz. decaf coffee | 8 oz. skim milk |
| | | 8 oz. decaf coffee |

Snack: 4 oz. diet popcorn  
Urine Test: 2 hrs. after breakfast - negative  
            2 hrs. after dinner - negative

05/05/92

Medication - ½ hr. before breakfast  
    3 units R - Humulin  
    b) 1 vasotec - 0.5 mg daily  
    c) 1 oz. orange juice - 2 hrs. after breakfast  
    d) 1 baby aspirin  
    e) 3 units - R - Humulin - ½ hr. before dinner

05/05/92 f) 1 oz. orange juice 2 hrs. after dinner

Menu

| Breakfast | Lunch | Dinner |
|---|---|---|
| 1 grapefruit | s.f. chicken soup | s.f beef soup |
| cooked cereal | 4 oz. baked fish | 8 oz. baked chicken |
| 2 egg whites only | 4 oz. seasoned rice | 4 oz. spinach |
| 1 bagel | 4 oz. diet peaches | 5 oz. baked potato |
| 4 oz. s.f. cheese | 8 oz. decaf coffee | 4 oz. diet jello |
| 4 oz. skim milk | 4 oz. skim milk | 8 oz. skim milk |
| 8 oz. decaf coffee | 2 slices bread | 8 oz. diet tea |
| diet applesauce | | |

Snack: s.f. popcorn  
Urine Test: 2 hrs. after breakfast - negative  
            2 hrs. after dinner - negative

05/06/92

Medication - ½ hr. before breakfast  
    3 units R - Humulin  
    b) 1 vasotec - 0.5 mg daily  
    c) 1 oz. orange juice - 2 hrs. after breakfast  
    d) 1 baby aspirin  
    e) 3 units - R - Humulin - ½ hr. before dinner  
    f) 1 oz. orange juice 2 hrs. after dinner

Menu

| Breakfast | Lunch | Dinner |
|---|---|---|
| 1 grapefruit | s.f chicken soup | s.f. beef soup |
| Special K cereal | 4 oz. Swiss cheese | 4 oz. baked ham |
| skim milk | 4 oz. s.f. crackers | 4 oz. sweet potatoes |
| 2 pancakes | 4 oz. green beans | 4 oz. rice |
| 2 oz. syrup | 4 oz. diet fruit cocktail | 4 oz. skim milk |
| 8 oz. skim milk | 8 oz. skim milk | 8 oz. diet tea |
| 8 oz. decaf coffee | 2 slices bread | 4 oz. diet jello |
| 4 oz. diet applesauce | | |
| diet applesauce | | |

Snack: 2 graham crackers  
        4 oz. skim milk  
        3 graham crackers  
        8 oz. skim milk Urine Test: 2 hrs. after breakfast - negative  
            2 hrs. after dinner - negative

05/07/92

Medication - ½ hr. before breakfast  
    3 units R - Humulin  
    b) 1 vasotec - 0.5 mg daily  
    c) 1 oz. orange juice - 2 hrs. after breakfast  
    d) 1 baby aspirin

05/07/92 -continued e) 3 units - R - Humulin - ½ hr. before dinner
f) 1 oz. orange juice 2 hrs. after dinner

Menu

| Breakfast | Lunch | Dinner |
|---|---|---|
| 1 grapefruit | s.f. chicken soup | s.f beef soup |
| Special K cereal | 4 oz. sweet potatoes | 2 salmon cakes |
| skim milk | 4 oz. broccoli | green beans |
| 4 oz. s.f. cheese | tuna salad mix | 4 oz. rice |
| 2 slices bread | lettuce/tomato | skim milk |
| diet applesauce | 2 slices bread | diet pears |
| skim milk | diet peaches | 8 oz. decaf coffee |
| 8 oz. decaf coffee | skim milk | |
| 2 pats s.f margarine | 8 oz. decaf coffee | |

Snack: 4 oz. diet popcorn

Urine Test: 2 hrs. after breakfast - negative
2 hrs. after dinner - negative

05/08/92

Medication - ½ hr. before breakfast
  3 units R - Humulin
  b) 1 vasotec - 0.5 mg daily
  c) 1 oz. orange juice - 2 hrs. after breakfast
  d) 1 baby aspirin
  e) 3 units - R - Humulin - ½ hr. before dinner
  f) 1 oz. orange juice 2 hrs. after dinner

Menu

| Breakfast | Lunch | Dinner |
|---|---|---|
| 1 grapefruit | s.f. beef soup | s.f. chicken soup |
| 4 oz. cooked cereal | tuna salad mix | 4 oz. s.f. pork chop |
| 1 bagel | lettuce/tomato | 4 oz. steamed cabbage |
| 4 oz. diet peaches | 4 oz. broccoli | 4 oz. oven baked fries |
| 8 oz. decaf coffee | 4 oz. diet pears | 4 oz. diet jello |
| skim milk | 8 oz. decaf coffee | 8 oz. diet tea |
| 2 salmon cakes | skim milk | |
| 2 oz. s.f. butter | 4 oz. s.f. crackers | |

Snack: 3 graham crackers
8 oz. skim milk

Urine Test: 2 hrs. after breakfast - negative
2 hrs. after dinner - negative

05/09/92

Medication - ½ hr. before breakfast
  3 units R - Humulin
  b) 1 vasotec - 0.5 mg daily
  c) 1 oz. orange juice - 2 hrs. after breakfast
  d) 1 baby aspirin
  e) 3 units - R - Humulin - ½ hr. before dinner
  f) 1 oz. orange juice 2 hrs. after dinner

Menu

| Breakfast | Lunch | Dinner |
|---|---|---|
| 1 grapefruit | s.f. chicken soup | s.f. beef bouillon |
| Special K cereal | 4 oz. diet tuna with diet mayonnaise | 4 oz. asparagus |
| 1 banana | 4 s.f. crackers | 4 oz. diet pears |
| 2 eg whites cooked | 4 oz. skim milk | 4 oz. skim milk |
| 1 bagel | 4 oz. diet fruits | 4 oz. diet soda |
| 2 oz. s.f. cheese | | |
| 8 oz. skim milk | | |
| 8 oz. decaf coffee | | |

Snack: 4 oz. diet popcorn

Urine Test: 2 hrs. after breakfast - negative
2 hrs. after dinner - negative

05/10/92

Medication - ½ hr. before breakfast
  3 units R - Humulin
  b) 1 vasotec - 0.5 mg
  c) 1 oz. orange juice - 2 hrs. after breakfast
  d) 1 baby aspirin
  e) 3 units - R - Humulin - ½ hr. before dinner
  f) 1 oz. orange juice 2 hrs. after dinner

Menu

| Breakfast | Lunch | Dinner |
|---|---|---|
| cooked grits | s.f. beef soup | s.f. turkey bouillon |
| 4 oz. salmon | 4 oz. s.f. cheddar cheese | 4 oz. cooked turkey |
| 2 slices bread | 4 oz. crackers | 4 oz. green beans |
| 4 oz. diet peaches | 4 oz. fresh fruit | 4 oz. seasoned rice |
| 4 oz. skim milk | 8 oz. skim milk | 4 oz. jello |
| 8 oz. decaf coffee | | 8 oz. diet iced tea |

Snack: 3 graham crackers
8 oz. skim milk

Urine Test: 2 hrs. after breakfast - negative
2 hrs. after dinner - negative

05/11/92

Medication - ½ hr. before breakfast
  3 units R - Humulin
  b) 1 vasotec - 0.5 mg
  c) 1 oz. orange juice - 2 hrs. after breakfast
  d) 1 baby aspirin
  e) 3 units - R - Humulin - ½ hr. before dinner
  f) 1 oz. orange juice 2 hrs. after dinner

Menu

| Breakfast | Lunch | Dinner |
|---|---|---|
| 1 grapefruit | s.f. bouillon | s.f. chicken soup |
| 8 oz. cooked cereal | salad | 4 oz. sliced turkey |
| 4 oz. salmon | lettuce and tomato | 4 oz. spinach |
| 4 oz. applesauce | 4 oz. s.f. cheddar cheese | 1 baked potato |
| 8 oz. skim milk | 4 oz. diet peaches | 4 oz. diet jello |
| 8 oz. decaf coffee | 4 oz. skim milk | 8 oz. iced tea w/Sweet & Low |
| | 8 oz. decaf coffee | 1 slice whole wheat bread |

Snack: s.f. popcorn

Urine Test: 2 hrs. after breakfast - negative
2 hrs. after dinner - negative

05/12/92

Medication - ½ hr. before breakfast
  3 units R - Humulin
  b) 1 vasotec - 0.5 mg
  c) 1 oz. orange juice - 2 hrs. after breakfast
  d) 1 baby aspirin
  e) 3 units - R - Humulin - ½ hr. before dinner
  f) 1 oz. orange juice 2 hrs. after dinner

Menu

| Breakfast | Lunch | Dinner |
|---|---|---|
| 1 grapefruit | s.f beef soup | s.f chicken soup |

-continued

05/12/92

| | | |
|---|---|---|
| 2 pancakes | baked fish | 8 oz. baked chicken |
| 2 oz. diet syrup | string beans | 4 oz. broccoli |
| 4 oz. fruit cocktail | 4 oz. rice | baked steak fries |
| 8 oz. skim milk | 8 oz. skim milk | 4 oz. diet jello |
| 8 oz. decaf coffee | 8 oz. decaf coffee w/ | 8 oz. iced tea |

-continued

05/12/92

| | |
|---|---|
| Sweet & Low | 8 oz. skim milk |
| Snack: graham crackers skim milk | Urine Test: 2 hrs. after breakfast - negative<br>2 hrs. after dinner - negative |

05/13/92

Medication - ½ hr. before breakfast
    3 units R - Humulin
  b) 1 vasotec - 0.5 mg
  c) 1 oz. orange juice - 2 hrs. after breakfast
  d) 1 baby aspirin
  e) 3 units - R - Humulin - ½ hr. before dinner
  f) 1 oz. orange juice 2 hrs. after dinner

Menu

| Breakfast | Lunch | Dinner |
|---|---|---|
| 1 grapefruit | s.f. beef soup | s.f. chicken soup |
| 4 oz. cooked cereal | 4 oz. salmon | 4 oz. pork chop |
| 2 hard cooked egg white (only) | 4 oz. cooked rice | 4 oz. steamed cabbage |
| 4 oz. s.f. cheddar cheese | 4 oz. green beans | 4 oz. mac/cheese (diet) |
| 4 oz. natural applesauce | 4 oz. shced peaches | 8 oz. iced tea |
| 8 oz. decaf coffee w/Sweet & Low | 1 slice whole wheat bread | 4 oz. diet jello |
| 4 oz. skim milk | 12 oz. diet soda | |
| 1 slice whole wheat bread | 4 oz. skim milk | |

| | |
|---|---|
| Snack: diet popcorn<br>8 oz. decaf coffee | Urine Test: 2 hrs. after breakfast - negative<br>2 hrs. after dinner - negative |

05/14/92

Medication - ½ hr. before breakfast
    3 units R - Humulin
  b) 1 vasotec - 0.5 mg
  c) 1 oz. orange juice - 2 hrs. after breakfast
  d) 1 baby aspirin
  e) 3 units - R - Humulin - ½ hr. before dinner
  f) 1 oz. orange juice 2 hrs. after dinner

Menu

| Breakfast | Lunch | Dinner |
|---|---|---|
| 1 grapefruit | s.f. beef soup | s.f. chicken soup |
| 4 oz. cooked grits | baked pork chop | baked halibut |
| 5 oz. fried fish | 4 oz. broccoli | 4 oz. steamed cabbage |
| 2 sliced whole wheat bread | 4 oz. s.f. macaroni & cheese | 4 oz. diet jello |
| 4 oz. natural applesauce | 4 oz. diet pears | 8 oz. diet tea |
| 8 oz. decaf coffee | 8 oz. decaf coffee w/Sweet & Low | 4 oz. skim milk |
| 4 oz. skim milk | | 2 slices whole wheat bread |

| | |
|---|---|
| Snack: diet popcorn | Urine Test: 2 hrs. after breakfast - negative<br>2 hrs. after dinner - negative |

05/15/92

| | |
|---|---|
| Medication - ½ hr. before breakfast<br>    3 units R - Humulin | 2 wks. doctor's appointment<br>call in 1 week | b) 1 vasotec - 0.5 mg
  c) 1 oz. orange juice - 2 hrs. after breakfast
  d) 1 baby aspirin
  e) 3 units - R - Humulin - ½ hr. before dinner
  f) 1 oz. orange juice 2 hrs. after dinner
Doctor appointment today
125/75 pressure
104 - blood test
Reduced to 2 units R for breakfast/2 units for dinner

Menu

| Breakfast | Lunch | Dinner |
|---|---|---|
| | | 2 units |
| ½ grapefruit | 4 oz. beef soup | 4 oz. s.f. chicken soup |
| 4 oz. cooked grits | 4 oz. sliced turkey | 4 oz. baked chicken |
| 4 oz. cooked salmon | 4 oz. cabbage | 4 oz. white rice |

05/15/92

| | | |
|---|---|---|
| 1 slice whole wheat bread | 4 oz. sweet potatoes | 4 oz. broccoli |
| 8 oz. decaf coffee | 8 oz. iced tea | 4 oz. skim milk |
| 4 oz. skim milk | | 8 oz. diet tea w/Sweet & Low |
| 1 oz. s.f. cheddar cheese | | 4 oz. jello |

Snack: 1 4 oz. bag diet popcorn    Urine Test: 2 hrs. after breakfast - negative
                                               2 hrs. after dinner - negative

05/16/92

Medication - ½ hr. before breakfast
   2 units R - Humulin
   b) 1 vasotec - 0.5 mg
   c) 1 oz. orange juice - 2 hrs. after breakfast
   d) 1 baby aspirin
   e) 2 units - R - Humulin - ½ hr. before dinner
   f) 1 oz. orange juice 2 hrs. after dinner

Menu

| Breakfast | Lunch | Dinner |
|---|---|---|
| ½ grapefruit | 4 oz. s.f. chicken soup bouillon | 4 oz. beef bouillon soup |
| 4 oz. skim milk | 3 oz. sardines | 8 oz. baked chicken |
| 1 bagel | 2 slices whole wheat bread | 4 oz. cooked carrots |
| 4 oz. s.f. cheese | 4 oz. tuna salad w/olive oil | 4 oz. broccoli |
| 4 oz. applesauce | 8 oz. skim milk | 8 oz. diet iced tea w/Sweet & Low |
| 8 oz. decaf coffee | 4 oz. canned diet fruits | 1 4 oz. diet jello |

Snack: diet popcorn    Urine Test: 2 hrs. after breakfast - negative
                                   2 hrs. after dinner - negative

05/17/92

Medication - ½ hr. before breakfast
   2 units R - Humulin
   b) 1 vasotec - 0.5 mg
   c) 1 oz. orange juice - 2 hrs. after breakfast
   d) 1 baby aspirin
   e) 2 units - R - Humulin - ½ hr. before dinner
   f) 1 oz. orange juice 2 hrs. after dinner

Menu

| Breakfast | Lunch | Dinner |
|---|---|---|
| 1 glass grapefruit juice | 4 oz. chicken bouillon soup | 4 oz. beef bouillon soup |
| 4 oz. oatmeal | 3 oz. peanut butter | baked halibut |
| 4 oz. skim milk | 2 slices whole wheat bread | 4 oz. rice |
| 1 egg white w/2 oz. s.f. cheese | 4 oz. tossed salad | 4 oz. green beans |
| 2 oz. fresh tomatoes | 4 oz. skim milk | 3 oz. tossed salad |
| 2 slices whole wheat toast | 4 oz. diet canned fruits | 8 oz. iced tea |
| 4 oz. applesauce | | 4 oz. diet jello |
| 8 oz. decaf coffee w/Sweet & Low | | |

Snack:  3 graham crackers    Urine Test: 2 hrs. after breakfast - negative
        w/skim milk                       2 hrs. after dinner - negative

05/18/92

Medication - ½ hr. before breakfast
   2 units R - Humulin
   b) 1 vasotec - 0.5 mg
   c) 1 oz. orange juice - 2 hrs. after breakfast
   d) 1 baby aspirin
   e) 2 units - R - Humulin - ½ hr. before dinner
   f) 1 oz. orange juice 2 hrs. after dinner

Menu

| Breakfast | Lunch | Dinner |
|---|---|---|
| ½ grapefruit | 4 oz. beef bouillon soup | 4 oz. chicken soup |
| 4 oz. cooked grits | 4 oz. cooked chicken | 4 oz. baked salmon steak |
| 3 oz. cooked port hash | 4 oz. corn | collard greens |
| 2 slices whole wheat bread | 4 oz. string beans | 3 oz. sweet potatoes |
| 4 oz. natural applesauce | 4 oz. diet canned fruit | 8 oz. iced tea w/Sweet & Low |
| | 4 oz. skim milk | 4 oz. skim milk |

|           |           |
|-----------|-----------|
| \-continued |         |
| 05/18/92  |           |

| 8 oz. decaf coffee | |
|---|---|
| Snack: 3 graham crackers<br>4 oz. skim milk | Urine Test: 2 hrs. after breakfast - negative<br>2 hrs. after dinner - negative |

| 05/19/92 |
|---|
| Medication - ½ hr. before breakfast<br>    2 units R - Humulin<br>  b) 1 vasotec - 0.5 mg<br>  c) 1 oz. orange juice - 2 hrs. after breakfast<br>  d) 1 baby aspirin<br>  e) 2 units - R - Humulin - ½ hr. before dinner<br>  f) 1 oz. orange juice 2 hrs. after dinner |

| Menu | | |
|---|---|---|
| Breakfast | Lunch | Dinner |
| 1 grapefruit | 4 oz. chicken soup | s.f. beef soup |
| 1 egg | 4 oz. sardines | 4 oz. pork chops |
| 3 oz. cheese | 2 slices whole wheat bread | 4 oz. broccoli |
| 2 slices whole wheat toast | w/tomato slices and lettuce | 1 ear corn on the cob |
| 4 oz. applesauce | 4 oz. skim milk | diet jello |
| 4 oz. skim milk | 4 oz. diet fruits | 8 oz. diet iced tea |
| 8 oz. decaf coffee | | 4 oz. tossed salad w/olive oil |

| | |
|---|---|
| Snack: 3 graham crackers<br>8 oz. skim milk | Urine Test: 2 hrs. after breakfast - negative<br>2 hrs. after dinner - negative |

| 05/20/92 |
|---|
| Medication - ½ hr. before breakfast<br>    2 units R - Humulin<br>  b) 1 vasotec - 0.5 mg<br>  c) 1 oz. orange juice - 2 hrs. after breakfast<br>  d) 1 baby aspirin<br>  e) 2 units - R - Humulin - ½ hr. before dinner<br>  f) 1 oz. orange juice 2 hrs. after dinner |

| Menu | | |
|---|---|---|
| Breakfast | Lunch | Dinner |
| ½ grapefruit | 4 oz. s.f. beef soup | 4 oz. s.f. chicken soup |
| 4 oz. cooked salmon | 4 oz. s.f. cheddar cheese | 4 oz. s.f. turkey |
| 2 oz. cooked grits | 4 s.f crackers | 4 oz. oven browned steak fries |
| 4 oz. applesauce | 4 oz. tossed salad w/olive oil | 4 oz. lettuce/tomato |
| 4 oz. skim milk | 4 oz. diet fruit | 4 oz. diet jello |
| 8 oz. decaf coffee w/Sweet & Low | 8 oz. skim milk | |

| | |
|---|---|
| Snack: 3 graham crackers<br>8 oz. skim milk | Urine Test: 2 hrs. after breakfast - negative<br>2 hrs. after dinner - negative |

| 05/21/92 |
|---|
| Medication - ½ hr. before breakfast<br>    2 units R - Humulin<br>  b) 1 vasotec - 0.5 mg<br>  c) 1 oz. orange juice - 2 hrs. after breakfast<br>  d) 1 baby aspirin<br>  e) 2 units - R - Humulin - ½ hr. before dinner<br>  f) 1 oz. orange juice 2 hrs. after dinner |

| Menu | | |
|---|---|---|
| Breakfast | Lunch | Dinner |
| ½ grapefruit | 4 oz. s.f. chicken bouillon | 4 oz. s.f. beef bouillon |
| 3 small pancakes | 6 oz. tuna fish salad | 4 oz. baked fish |
| 2 oz. diet syrup | w/diet mayonnaise | 4 oz. baked steak fried potatoes |
| 4 oz. skim milk | 4 s.f. crackers | 4 oz. spinach |
| 8 oz. decaf coffee w/Sweet & Low | 8 oz. skim milk | 4 oz. diet jello |
| 4 oz. applesauce | 4 oz. diet fruit | 8 oz. diet tea w/Sweet & Low |

| | |
|---|---|
| Snack: 2 graham crackers<br>    1 oz. s.f. peanut butter<br>    8 oz. skim milk | Urine Test: 2 hrs. after breakfast - negative<br>2 hrs. after dinner - negative |

| 05/22/92 | | |
|---|---|---|
| Medication - ½ hr. before breakfast  2 units R - Humulin  b) 1 vasotec - 0.5 mg  c) 1 oz. orange juice - 2 hrs. after breakfast  d) 1 baby aspirin  e) 2 units - R - Humulin - ½ hr. before dinner  f) 1 oz. orange juice 2 hrs. after dinner | | |
| Menu | | |
| Breakfast | Lunch | Dinner |
| 1 grapefruit  omelette made from 1 oz. s.f. cheddar cheese, ½ fresh tomato, 1 egg and diced onion  2 slices whole wheat toast  4 oz. applesauce  4 oz. skim milk  8 oz. decaf coffee | 4 oz. s.f. beef soup  2 chicken hot dogs on rolls w/onion and mustard  4 oz. tossed salad  4 oz. diet fruit  8 oz. skim milk | s.f chicken soup  4 oz. tuna fish salad  4 crackers  4 oz. cole slaw  4 oz. diet jello  8 oz. diet tea w/Sweet & Low |
| Snack: 2 graham crackers  1 oz. s.f. peanut butter  8 oz. skim milk | Urine Test: 2 hrs. after breakfast - negative  2 hrs. after dinner - negative | |

| 05/23/92 | | |
|---|---|---|
| Medication - ½ hr. before breakfast  1 unit R - Humulin  b) 1 vasotec - 0.5 mg  c) 1 oz. orange juice - 2 hrs. after breakfast  d) 1 baby aspirin  e) 1 unit - R - Humulin - ½ hr. before dinner  f) 1 oz. orange juice 2 hrs. after dinner | Medication reduced to 1 unit | |
| Menu | | |
| Breakfast | Lunch | Dinner |
| ½ grapefruit  cooked oatmeal  4 oz. skim milk  4 oz. s.f. cheddar cheese  4 crackers  4 oz. natural applesauce  8 oz. decaf coffee | 4 oz. s.f. beef soup  tuna salad platter  beet salad  8 oz. skim milk  diet fruit  4 s.f. crackers | 4 oz. chicken soup  baked turkey  3 oz. sweet potatoes  4 oz. spinach  8 oz. diet tea w/Sweet & Low  4 oz. jello |
| Snack: 4 oz. s.f. popcorn | Urine Test: 2 hrs. after breakfast - negative  2 hrs. after dinner - negative | |

| 05/24/92 | | |
|---|---|---|
| Medication - ½ hr. before breakfast  1 unit R - Humulin  b) 1 vasotec - 0.5 mg  c) 1 oz. orange juice - 2 hrs. after breakfast  d) 1 baby aspirin  e) 1 unit - R - Humulin - ½ hr. before dinner  f) 1 oz. orange juice 2 hrs. after dinner | | |
| Menu | | |
| Breakfast | Lunch | Dinner |
| 1 grapefruit  1 bagel  natural jelly (no sugar)  4 oz. cooked oatmeal  4 oz. skim milk  8 oz. decaf coffee  4 oz. applesauce | 4 oz. s.f. chicken soup  4 oz. sliced turkey  2 slices whole wheat bread  s.f diet mayonnaise  4 oz. tossed salad  4 oz. skim milk  4 oz. diet fruits  8 oz. decaf coffee | 4 oz. s.f. beef soup  4 oz. roast pork  4 oz. sweet potatoes  4 oz. collard greens  2 oz. corn bread  8 oz. diet tea w/Sweet & Low  4 oz. diet jello |
| Snack: 3 graham crackers  8 oz. skim milk | Urine Test: 2 hrs. after breakfast - negative  2 hrs. after dinner - negative | |

| 05/25/92 |
|---|
| Medication - ½ hr. before breakfast  R - Humulin  b) 1 vasotec - 0.5 mg |

-continued

05/25/92 c) 1 oz. orange juice - 2 hrs. after breakfast
    d) 1 baby aspirin
    e) 1 unit - R - Humulin - ½ hr. before dinner
    f) 1 oz. orange juice 2 hrs. after dinner

Menu

| Breakfast | Lunch | Dinner |
|---|---|---|
| 1 grapefruit | 4 oz. s.f. beef soup | 4 oz. s.f. chicken soup |
| 4 oz. cooked oatmeal | 4 oz. sardines | 4 oz. baked chicken |
| 1 bagel | 4 oz. crackers | 4 oz. white rice |
| 4 oz. s.f. cheddar cheese | ½ oz. sliced onions | 4 oz. broccoli |
| 4 oz. applesauce | mustard | 4 oz. diet jello |
| 4 oz. skim milk | 4 oz. diet fruits | 8 oz. diet tea w/Sweet & Low |
| 8 oz. decaf coffee | 8 oz. decaf coffee | 4 oz. tossed salad |

Snack: 2 graham crackers     Urine Test: 2 hrs. after breakfast - negative
       8 oz. skim milk                      2 hrs. after dinner - negative

05/26/92

Medication - ½ hr. before breakfast
    1 unit R - Humulin
    b) 1 vasotec - 0.5 mg
    c) 1 oz. orange juice - 2 hrs. after breakfast
    d) 1 baby aspirin
    e) 1 unit - R - Humulin - ½ hr. before dinner
    f) 1 oz. orange juice 2 hrs. after dinner

Menu

| Breakfast | Lunch | Dinner |
|---|---|---|
| 1 grapefruit | 4 oz. s.f. beef soup | 4 oz. s.f. chicken soup |
| 4 oz. cornflakes | 4 oz. sliced turkey | baked flounder |
| 12 raisins | lettuce/tomatoes | seasoned corn |
| 4 oz. skim milk | 2 slices whole wheat bread | 4 oz. broccoli |
| 4 oz. applesauce | 1 oz. s.f. mayonnaise | 4 oz. tossed salad |
| 8 oz. decaf coffee | 4 oz. diet fruits | 4 oz. diet jello |
|  | 8 oz. decaf coffee | 8 oz. diet tea |

Snack: 3 graham crackers     Urine Test: 2 hrs. after breakfast - negative
       8 oz. skim milk                      2 hrs. after dinner - negative

05/27/92

Medication - ½ hr. before breakfast
    1 unit R - Humulin
    b) 1 vasotec - 0.5 mg
    c) 1 oz. orange juice - 2 hrs. after breakfast
    d) 1 baby aspirin
    e) 1 unit - R - Humulin - ½ hr. before dinner
    f) 1 oz. orange juice 2 hrs. after dinner

Menu

| Breakfast | Lunch | Dinner |
|---|---|---|
| 1 grapefruit | 4 oz. s.f. chicken soup | 4 oz. s.f. beef soup |
| 4 oz. cooked oatmeal | 4 oz. salmon salad | 4 oz. pork chops |
| 4 oz. skim milk | 4 oz. lettuce/tomato | 4 oz. applesauce |
| 4 oz. applesauce | 4 oz. diet fruits | 4 oz. string bean |
| 8 oz. decaf coffee w/skim milk & Sweet & Low | 8 oz. skim milk | 4 oz. diet fruits |
|  |  | 2 slices whole wheat bread |
|  |  | 8 oz. diet tea w/Sweet & Low |

Snack: 3 graham crackers     Urine Test: 2 hrs. after breakfast - negative
       8 oz. skim milk                      2 hrs. after dinner - negative

05/28/92

Medication - ½ hr. before breakfast
    1 unit R - Humulin
    b) 1 vasotec - 0.5 mg
    c) 1 oz. orange juice - 2 hrs. after breakfast
    d) 1 baby aspirin
    e) 1 unit - R - Humulin - ½ hr. before dinner
    f) 1 oz. orange juice 2 hrs. after dinner

Menu

| Breakfast | Lunch | Dinner |
|---|---|---|
| 1 grapefruit | 4 oz. s.f. chicken soup | 4 oz. s.f. beef soup |
| 4 oz. cornflakes | s.f. peanut butter on whole wheat bread with natural jelly | 4 oz. sliced beef (no fat) |
| ½ banana |  | 4 oz. oven baked french fries |
| 4 oz. skim milk | 1 fresh peach | 4 oz. spinach |
| 4 oz. natural applesauce | 4 oz. skim milk | 4 oz. tossed salad |
| 8 oz. decaf coffee |  | 4 oz. diet jello |
|  |  | 8 oz. diet tea w/Sweet & Low |

| | |
|---|---|
| \multicolumn{2}{c}{-continued} |
| \multicolumn{2}{c}{05/28/92} |
| Snack: 4 oz. s.f. popcorn | Urine Test: 2 hrs. after breakfast - negative |
| | 2 hrs. after dinner - negative |

05/29/92

Medication - ½ hr. before breakfast
      1 unit R - Humulin
   b) 1 vasotec - 0.5 mg
   c) 1 oz. orange juice - 2 hrs. after breakfast
   d) 1 baby aspirin
   e) 1 unit - R - Humulin - ½ hr. before dinner
   f) 1 oz. orange juice 2 hrs. after dinner

Menu

| Breakfast | Lunch | Dinner |
|---|---|---|
| ½ grapefruit | 4 oz. s.f. bouillon soup | 4 oz. s.f beef soup |
| 4 oz. cooked oatmeal | 4 oz. sardines | 8 oz. baked chicken |
| 4 oz. s.f. cheddar cheese | 4 crackers | 4 oz. broccoli |
| 4 s.f crackers | lettuce/tomato salad w/olive oil | 4 oz. white rice |
| 4 oz. natural applesauce | 8 oz. skim milk | 4 oz. tossed salad w/olive oil |
| 4 oz. skim milk | | 8 oz. iced tea w/Sweet & Low |
| 8 oz. decaf coffee w/Sweet & Low | | 4 oz. diet jello |

| | |
|---|---|
| Snack: 3 graham crackers | Urine Test: 2 hrs. after breakfast - negative |
|       8 oz. skim milk | 2 hrs. after dinner - negative |

05/30/92

Medication - ½ hr. before breakfast
      1 unit R - Humulin
   b) 1 vasotec - 0.5 mg
   c) 1 oz. orange juice - 2 hrs. after breakfast
   d) 1 baby aspirin
   e) 1 unit - R - Humulin - ½ hr. before dinner
   f) 1 oz. orange juice 2 hrs. after dinner

Menu

| Breakfast | Lunch | Dinner |
|---|---|---|
| ½ grapefruit | 4 oz. s.f. chicken soup | 4 oz. s.f. beef soup |
| 2 pancakes | 4 oz. sliced turkey | 4 oz. baked fish |
| 2 oz. diet syrup | 2 slices whole wheat bread | 4 oz. green beans |
| 4 oz. applesauce | 4 oz. tossed salad | 4 oz. white rice |
| 4 oz. skim milk | 8 oz. skim milk | 4 oz. diet jello |
| 8 oz. decaf coffee w/Sweet & Low | 4 oz. diet fruit | 8 oz. iced tea w/Sweet & Low |

| | |
|---|---|
| Snack: 4 oz. s.f. popcorn | Urine Test: 2 hrs. after breakfast - negative |
| | 2 hrs. after dinner - negative |

05/31/92

Medication - ½ hr. before breakfast
      1 unit R - Humulin
   b) 1 vasotec - 0.5 mg
   c) 1 oz. orange juice - 2 hrs. after breakfast
   d) 1 baby aspirin
   e) 1 unit - R - Humulin - ½ hr. before dinner
   f) 1 oz. orange juice 2 hrs. after dinner

Menu

| Breakfast | Lunch | Dinner |
|---|---|---|
| 4 oz. oatmeal | 4 oz. s.f. chicken soup | 4 oz. s.f. beef soup |
| 1 egg | 4 oz. pork chops | 4 oz. baked chicken wings |
| 2 oz. s.f. cheese | 4 oz. tossed salad | 4 oz. white rice |
| 1 tomato | 4 oz. broccoli | 4 oz. spinach |
| ½ onion for omelette | 4 oz. skim milk | 4 oz. skim milk |
| 4 oz. natural applesauce | 4 oz. diet fruits | 8 oz. diet tea w/Sweet & Low |
| 8 oz. skim milk | | 4 oz. diet jello |
| 2 slices whole wheat bread w/unsalted butter | | |

| | |
|---|---|
| Snack: 3 graham crackers | Urine Test: 2 hrs. after breakfast - negative |

-continued

| 05/31/92 | |
|---|---|
| 8 oz. skim milk | 2 hrs. after dinner - negative |

| 06/01/92 | |
|---|---|
| Medication - ALL INSULIN STOPPED TODAY | |
| a) 1 vasotec - 0.1 mg | |
| b) 1 baby aspirin | |
| Menu | |
| 1500 calories - low fat, low cholesterol diet | |
| Snack: 4 oz. popcorn | Urine Test: 2 hrs. after breakfast - negative<br>2 hrs. after dinner - negative |

| 06/02/92 | |
|---|---|
| Medication - a) 1 vasotec - 0.1 mg | |
| b) 1 baby aspirin | |
| Menu | |
| 1500 calories - low fat, low cholesterol diet | |
| Snack: 3 graham crackers<br>8 oz. skim milk | Urine Test: 2 hrs. after breakfast - negative<br>2 hrs. after dinner - negative |

| 06/03/92 | |
|---|---|
| Medication - a) 1 vasotec - 0.1 mg | |
| b) 1 baby aspirin | |
| Menu | |
| 1500 calories - low fat, low cholesterol diet | |
| Snack: 3 sticks celery<br>w/2 oz. peanut butter | Urine Test: 2 hrs. after breakfast - negative<br>2 hrs. after dinner - negative |

| 06/04/92 | |
|---|---|
| Medication - a) 1 vasotec - 0.1 mg | |
| b) 1 baby aspirin | |
| Menu | |
| 1500 calories - low fat, low cholesterol diet | |
| Snack: 3 graham crackers<br>8 oz. skim milk | Urine Test: 2 hrs. after breakfast - negative<br>2 hrs. after dinner - negative |

| 06/05/92 | |
|---|---|
| Medication - a) 1 vasotec - 0.1 mg | |
| b) 1 baby aspirin | |
| Menu | |
| 1500 calories - low fat, low cholesterol diet | |
| Snack: 3 carrot sticks<br>2 oz. peanut butter | Urine Test: 2 hrs. after breakfast - negative<br>2 hrs. after dinner - negative |

| 06/06/92 | |
|---|---|
| Medication - a) 1 vasotec - 0.1 mg | |
| b) 1 baby aspirin | |
| Menu | |

-continued

| 06/06/92 | |
|---|---|
| 1500 calories - low fat, low cholesterol diet | |
| Snack: 3 graham crackers<br>8 oz. skim milk | Urine Test: 2 hrs. after breakfast - negative<br>2 hrs. after dinner - negative |

| 06/07/92 | |
|---|---|
| Medication - a) 1 vasotec - 0.1 mg | |
| b) 1 baby aspirin | |
| Menu | |
| 1500 calories - low fat, low cholesterol diet | |
| Snack:<br>4 oz. diet popcorn | Urine Test: 2 hrs. after breakfast - negative<br>2 hrs. after dinner - negative |

| 06/08/92 | |
|---|---|
| Medication - a) 1 vasotec - 0.1 mg | |
| b) 1 baby aspirin | |
| Menu | |
| 1500 calories - low fat, low cholesterol diet | |
| Snack: 3 pieces celery<br>2 oz. peanut butter | Urine Test: 2 hrs. after breakfast - negative<br>2 hrs. after dinner - negative |

| 06/09/92 | |
|---|---|
| Medication - a) 1 vasotec - 0.1 mg | |
| b) 1 baby aspirin | |
| Menu | |
| 1500 calories - low fat, low cholesterol diet | |
| Snack: 3 graham crackers<br>8 oz. skim milk | Urine Test: 2 hrs. after breakfast - negative<br>2 hrs. after dinner - negative |

| 06/10/92 | |
|---|---|
| Medication - a) 1 vasotec - 0.1 mg | |
| b) 1 baby aspirin | |
| Menu | |
| 1500 calories - low fat, low cholesterol diet | |
| Snack: 4 oz. popcorn | Urine Test: 2 hrs. after breakfast - negative<br>2 hrs. after dinner - negative |

| 06/11/92 | |
|---|---|
| Medication - a) 1 vasotec - 0.1 mg | |
| b) 1 baby aspirin | |
| Menu | |
| 1500 calories - low fat, low cholesterol diet | |
| Snack: 3 pieces celery<br>2 oz. peanut butter | Urine Test: 2 hrs. after breakfast - negative<br>2 hrs. after dinner - negative |

| 06/12/92 |
|---|
| Medication - a) 1 vasotec - 0.1 mg<br>b) 1 baby aspirin |
| Menu |
| 1500 calories - low fat, low cholesterol diet |
| Snack: 3 graham crackers / 8 oz. skim milk    Urine Test: 2 hrs. after breakfast - negative / 2 hrs. after dinner - negative |

| 06/13/92 |
|---|
| Medication - a) 1 vasotec - 0.1 mg<br>b) 1 baby aspirin |
| Menu |
| 1500 calories - low fat, low cholesterol diet |
| Snack: 4 oz. popcorn    Urine Test: 2 hrs. after breakfast - negative / 2 hrs. after dinner - negative |

| 06/14/92 |
|---|
| Medication - a) 1 vasotec - 0.1 mg<br>b) 1 baby aspirin |
| Menu |
| 1500 calories - low fat, low cholesterol diet |
| Snack: 3 carrot sticks w/2 oz. peanut butter    Urine Test: 2 hrs. after breakfast - negative / 2 hrs. after dinner - negative |

| 06/15/92 |
|---|
| Medication - a) 1 vasotec - 0.1 mg<br>b) 1 baby aspirin |
| Menu |
| 1500 calories - low fat, low cholesterol diet |
| Snack: 3 graham crackers / 8 oz. skim milk    Urine Test: 2 hrs. after breakfast - negative / 2 hrs. after dinner - negative |

| 06/16/92 |
|---|
| Medication - a) 1 vasotec - 0.1 mg<br>b) 1 baby aspirin |
| Menu |
| 1500 calories - low fat, low cholesterol diet |
| Snack: 4 oz. popcorn    Urine Test: 2 hrs. after breakfast - negative / 2 hrs. after dinner - negative |

| 06/17/92 |
|---|
| Medication - a) 1 vasotec - 0.1 mg<br>b) 1 baby aspirin |
| Menu |
| 1500 calories - low fat, low cholesterol diet |
| Snack: 3 celery sticks / 2 oz. peanut butter    Urine Test: 2 hrs. after breakfast - negative / 2 hrs. after dinner - negative |

| 06/18/92 |
|---|
| Medication - a) 1 vasotec - 0.1 mg<br>b) 1 baby aspirin |
| Menu |
| 1500 calories - low fat, low cholesterol diet |
| Snack: 3 graham crackers / 8 oz. skim milk    Urine Test: 2 hrs. after breakfast - negative / 2 hrs. after dinner - negative |

| 06/19/92 |
|---|
| Medication - a) 1 vasotec - 0.1 mg<br>b) 1 baby aspirin |
| Menu |
| 1500 calories - low fat, low cholesterol diet |
| Snack: 4 oz. popcorn    Urine Test: 2 hrs. after breakfast - negative / 2 hrs. after dinner - negative |

| 06/21/92 |
|---|
| Medication - a) 1 vasotec - 0.1 mg<br>b) 1 baby aspirin |
| Menu |
| 1500 calories - low fat, low cholesterol diet |
| Snack: 3 graham crackers / 8 oz. skim milk    Urine Test: 2 hrs. after breakfast - negative / 2 hrs. after dinner - negative |

| 06/23/92 |
|---|
| Medication - a) 1 vasotec - 0.1 mg<br>b) 1 baby aspirin |
| Menu |
| 1500 calories - low fat, low cholesterol diet |
| Snack: 3 graham crackers / 8 oz. skim milk    Urine Test: 2 hrs. after breakfast - negative / 2 hrs. after dinner - negative |

| 06/25/92 |
|---|
| Medication - a) 1 vasotec - 0.1 mg<br>b) 1 baby aspirin |
| Menu |
| 1500 calories - low fat, low cholesterol diet |
| Snack: 3 carrot sticks w/2 oz. peanut butter    Urine Test: 2 hrs. after breakfast - negative / 2 hrs. after dinner - negative |

| 06/26/92 |
|---|
| Medication - a) 1 vasotec - 0.1 mg<br>b) 1 baby aspirin |
| Menu |
| 1500 calories - low fat, low cholesterol diet |
| Snack: 3 graham crackers / 8 oz. skim milk    Urine Test: 2 hrs. after breakfast - negative / 2 hrs. after dinner - negative |

| 06/27/92 |
|---|
| Medication - a) 1 vasotec - 0.1 mg<br>b) 1 baby aspirin |
| Menu |
| 1500 calories - low fat, low cholesterol diet |
| Snack: 3 celery sticks    Urine Test: 2 hrs. after breakfast - negative<br>2 oz. peanut butter                  2 hrs. after dinner - negative |

| 06/28/92 |
|---|
| Medication - a) 1 vasotec - 0.1 mg<br>b) 1 baby aspirin |
| Menu |
| 1500 calories - low fat, low cholesterol diet |
| Snack: 4 oz. s.f. popcorn    Urine Test: 2 hrs. after breakfast - negative<br>                                    2 hrs. after dinner - negative |

| 06/29/92 |
|---|
| Medication - a) 1 vasotec - 0.1 mg<br>b) 1 baby aspirin |
| Menu |
| 1500 calories - low fat, low cholesterol diet |
| Snack: 3 graham crackers    Urine Test: 2 hrs. after breakfast - negative<br>8 oz. skim milk                2 hrs. after dinner - negative |

| 06/30/92 |
|---|
| Medication - a) 1 vasotec - 0.1 mg<br>b) 1 baby aspirin |
| Menu |
| 1500 calories - low fat, low cholesterol diet |
| Snack: 3 celery sticks    Urine Test: 2 hrs. after breakfast - negative<br>2 oz. peanut butter                    2 hrs. after dinner - negative |

| 07/01/92 |
|---|
| Medication - a) 1 vasotec - 0.1 mg<br>b) 1 baby aspirin |
| Menu |
| 1500 calories - low fat, low cholesterol diet |
| Snack: 3 graham crackers    Urine Test: 2 hrs. after breakfast - negative<br>8 oz. skim milk                2 hrs. after dinner - negative |

| 07/02/92 |
|---|
| Medication - a) 1 vasotec - 0.1 mg<br>b) 1 baby aspirin |
| Menu |
| 1500 calories - low fat, low cholesterol diet |
| Snack: 4 oz. s.f. popcorn    Urine Test: 2 hrs. after breakfast - negative<br>                                    2 hrs. after dinner - negative |

| 07/03/92 |
|---|
| Medication - a) 1 vasotec - 0.1 mg<br>b) 1 baby aspirin |
| Menu |
| 1500 calories - low fat, low cholesterol diet |
| Snack: 3 carrot sticks    Urine Test: 2 hrs. after breakfast - negative<br>2 oz. peanut butter                  2 hrs. after dinner - negative |

| 07/04/92 |
|---|
| Medication - a) 1 vasotec - 0.1 mg<br>b) 1 baby aspirin |
| Menu |
| 1500 calories - low fat, low cholesterol diet |
| Snack: 3 graham crackers    Urine Test: 2 hrs. after breakfast - negative<br>8 oz. skim milk                2 hrs. after dinner - negative |

| 07/05/92 |
|---|
| Medication - a) 1 vasotec - 0.1 mg<br>b) 1 baby aspirin |
| Menu |
| 1500 calories - low fat, low cholesterol diet |
| Snack: 3 carrot sticks    Urine Test: 2 hrs. after breakfast - negative<br>2 oz. peanut butter                  2 hrs. after dinner - negative |

| 07/06/92 |
|---|
| Medication - a) 1 vasotec - 0.1 mg<br>b) 1 baby aspirin |
| Menu |
| 1500 calories - low fat, low cholesterol diet |
| Snack: 3 celery sticks    Urine Test: 2 hrs. after breakfast - negative<br>2 oz. peanut butter                  2 hrs. after dinner - negative |

| 07/07/92 |
|---|
| Medication - a) 1 vasotec - 0.1 mg<br>b) 1 baby aspirin |
| Menu |
| 1500 calories - low fat, low cholesterol diet |
| Snack: 3 graham crackers    Urine Test: 2 hrs. after breakfast - negative<br>8 oz. skim milk                2 hrs. after dinner - negative |

| 07/08/92 |
|---|
| Medication - a) 1 vasotec - 0.1 mg<br>b) 1 baby aspirin |
| Menu |
| 1500 calories - low fat, low cholesterol diet |
| Snack: 4 oz. applesauce    Urine Test: 2 hrs. after breakfast - negative<br>3 graham crackers               2 hrs. after dinner - negative |

| 07/09/92 | |
|---|---|
| Medication - a) 1 vasotec - 0.1 mg  b) 1 baby aspirin | |
| Menu | |
| 1500 calories - low fat, low cholesterol diet | |
| Snack: 4 oz. s.f. popcorn | Urine Test: 2 hrs. after breakfast - negative  2 hrs. after dinner - negative |

| 07/10/92 | |
|---|---|
| Medication - a) 1 vasotec - 0.1 mg  b) 1 baby aspirin | |
| Menu | |
| 1500 calories - low fat, low cholesterol diet | |
| Snack: 4 oz. applesauce  3 graham crackers | Urine Test: 2 hrs. after breakfast - negative  2 hrs. after dinner - negative |

| 07/11/92 | |
|---|---|
| Medication - a) 1 vasotec - 0.1 mg  b) 1 baby aspirin | |
| Menu | |

-continued

| 07/11/92 | |
|---|---|
| 1500 calories - low fat, low cholesterol diet | |
| Snack: 4 oz. diet fruit  3 graham crackers | Urine Test: 2 hrs. after breakfast - negative  2 hrs. after dinner - negative |

| 07/12/92 | |
|---|---|
| Medication - a) 1 vasotec - 0.1 mg  b) 1 baby aspirin | |
| Menu | |
| 1500 calories - low fat, low cholesterol diet | |
| Snack: 4 oz. diet jello  3 graham crackers  8 oz. skim milk | Urine Test: 2 hrs. after breakfast - negative  2 hrs. after dinner - negative |

| 07/14/92 | |
|---|---|
| Medication - a) 1 vasotec - 0.1 mg  b) 1 baby aspirin | |
| Menu | |
| 1500 calories - low fat, low cholesterol diet | |
| Snack: | Urine Test: 2 hrs. after breakfast - negative |

F.M.
MEDICATION AND I.V. FLUID ORDERS
(DOSE ROUTE FREQUENCY)
PHARMACY
ORDERS (SET 1) Feldene DATE
TIME Insulin as follows:
S.C 4 u Humulin reg. 7
S.C 4 u Humulin NPH Stat
HUMULIN
5 u NPH
5 u reg - ½ hr. before breakfast
3 u reg - ½ hr. before lunch
4 u NPH
4 u reg - ½ hr. before supper
PHARMACY
ORDERS (SET 2) Feldene
DATE
TIME 12/7/91
(1) Condition 60 mg/O QID
(2) Zantac 150 mg/O BIN
1 m Compazine 10 mg stat
IVPB Zantac 50 mg Q 8
12 po zantac
12/8/91
(1) Tapor HIV nitroglycerin at 4 hrs.
(2) Nitroglycera ointment 111 g 6 h
12/8/91 - Insulin as follows:
5 u NPH
5 u reg - ½ hr. before supper
6 u NPH
6 u reg - ½ hr. before breakfast
4 u reg - ½ hr. before lunch
12/8/91
1 oppressor 25 mg PO
12/9
Increase heparin drip to 1100 'u' for = 22 echlers
2/10/91
Increase heparin drip to 24 cc hr. = 1200 'u'
2/10/91

NON MEDICATION ORDERS

1. Light diet for 1 day and then soft diet as follows:
CHO 180 gm

Port - 60 g
Fab 45 g - ½, ⅓, ⅓
2. Finger test for blood sugar 4×/day, before each meal and qho 1) In addition to finger test for sugar (as before) test urine for sugar 7×/day as follows:
before each meal, 2 hours afer each meal and at bedtime

| | | |
|---|---|---|
| | Have a container of chilled o.j. at her bed | |
| | 2) orange juice as follows: | |
| | if urine test 2 hours after a meal and at bedtime | |
| | is negative give 2 ounces, if 1/10% give 1 oz., if | |
| | higher, given nothing | |
| | 3) Divide her food into 3 meals. No snacks are | |
| | to be given at any time (only the juice as | |
| | ordered) | |
| | 4) Teach her to do her own urine tests and taker | |
| | her ___ accordingly | |
| 12/11/91 | | |
| 12/11/91 | | |
| 12/11/91 Insulin as follows: | 1) Kindly continue to let her do her urine tests | |
| 5 u NPH | and also have chilled o.j. at her bedtime to take | |
| 5 u reg ½ hr. before breakfast | as ordered. | |
| 3 u reg - ½ hr. before lunch | 2) Make sure she does not take a bedtime snack. | |
| 4 u reg | | |
| 4 u NPH - ½ hr. before supper | | |
| 12/12 | Kindly have a chilled container of o.j. at her | |
| | bedside from morning to bedtime every day. | |
| 12/13/91 | D/C daily Pt, PTI | |
| Zantac 150 mg PO BID | | |
| 12/13/91 | May be up and about | |
| Reduce insulin as follows: | Reduce o.j. supplement as follows: | |
| 4 u NPH | If urine test 2 hours after a meal or at bedtime is | |
| 4 u reg ½ hr. before breakfast | negative, give 1 oz. of juice | |
| 2 u reg. ½ hr. before lunch | If test is 1/10% - do not give any juice | |
| 3 u reg. | Repeat EKG on 12/16 | |
| 3 u NPH ½ hr. before supper | T.O. Dr. Shohet is gone | |
| | Patient may be transferred off floor | |
| 12/15/91 | | |
| Insulin as follows: | | |
| 5 u NPH | | |
| 5 u reg ½ hr. before breakfast | | |
| 3 u reg ½ hr. before lunch | | |

| | | | | |
|---|---|---|---|---|
| Wednesday, January 29 | | | morning | neg |
| before breakfast | negative | | after breakfast | n/a |
| 10 am | neg | | mid morn | ¼ |
| after lunch | neg | | after lunch | neg |
| before supper | neg | | mid afternoon | neg |
| after supper | neg | | before supper | neg |
| 10:30 pm | neg | | after supper | neg |
| if neg - 2 oz. | | | before bed | |
| if one - 1 oz. | | | Tuesday, February 4 | |
| Thursday, January 30 | | | morn | neg |
| morn | neg | | mid morning | neg |
| 10 am | 1/10 | | before lunch | neg |
| 12:15 before lunch | 1/4 | | after lunch | neg |
| 2:30 | neg | | mid afternoon | neg |
| before supper 5 pm | neg | | before supper | neg |
| 8:30 | 1/10 | | after supper | ¼ |
| last | neg | | before bedtime | ¼ |
| Friday, January 31 | | | Wednesday, February 5 | |
| morn 8:30 | neg | | before morning | ¼-2 normal |
| 10 am | neg | | mid morning | ¼ |
| before lunch | neg | | before lunch | neg |
| after lunch | neg | | after lunch | neg |
| before supper | neg | | mid afternoon | neg |
| after supper | neg | | before supper | neg |
| at night | neg | | after supper | 1/10 |
| Saturday, February 1 | | | before bed | 1/10 |
| before breakfast 8 am | neg | | Thursday, February 6 | |
| mid morn | neg | | before | neg |
| before lunch | neg | | after breakfast | ¼ |
| 2 hours later | neg | | before lunch | ¼ |
| before supper | | | after lunch | neg |
| 2 hours after supper | neg | | 2 hours after lunch | |
| before bed | neg | | before supper | neg |
| Sunday, February 2 | | | after supper | neg |
| am morn | neg | | before bed | neg |
| mid morn | neg | | Friday, February 7 | |
| after lunch | neg | | before breakfast | neg |
| mid afternoon | neg | | after breakfast | ¼ |
| before supper | neg | | before lunch | |
| after supper | neg | | after lunch | ¼ |
| before bed | neg | | before supper | ¼ |
| Monday, February 3 | | | after supper | ¼ |

-continued

| | |
|---|---|
| before bed | ¼ |
| Saturday, February 8 | |
| before breakfast | neg |
| before lunch | ¼ |
| after lunch | ¼ |
| before supper | neg |
| after supper | ¼ |
| 8 pm | ¼ |
| before bed | ¼ |
| Sunday, February 9 | |
| before breakfast | neg |
| after breakfast | ¼ |
| before lunch | ¼ |
| after lunch | ½ |
| before supper | reg |
| after supper | ¼ |
| before bedtime | ¼ |
| Monday, February 10 | |
| before breakfast | neg |
| after breakfast | |
| before lunch | neg |
| after lunch | neg |
| before supper | neg |
| after supper | ¼ |
| before bedtime | ¼ |
| Tuesday, February 11 | |
| before breakfast | neg |
| after breakfast | ¼ |
| before lunch | ¼ |
| after lunch | neg |
| before supper | neg |
| after supper | neg |
| Wednesday, February 12 | |
| before breakfast | neg |
| after breakfast | ¼ |
| before lunch | neg |
| after lunch | neg |
| before supper | neg |
| after supper | neg |
| before bed | |
| Thursday, February 13 | |
| before breakfast | neg |
| after breakfast | 1 ¼ |
| before lunch | neg |
| after lunch | ¼ |
| before supper | ¼ |
| after supper | neg |
| before bed | neg |
| Friday, February 14 | |
| before breakfast | neg |
| after breakfast | ¼ |
| before lunch | neg |
| after lunch | neg |
| before supper | neg |
| after supper | ¼ |
| before bed | ¼ |
| Saturday, February 15 | |
| before breakfast | neg |
| after breakfast | forgot |
| before lunch | neg |
| after lunch | neg |
| before supper | neg |
| after supper | neg |
| before bed | neg |
| Sunday, February 16 | |
| before breakfast | neg |
| after breakfast | ¼ |
| before lunch | neg |
| after lunch | neg |
| before supper | |
| after supper | neg |
| before bed | neg |
| Monday, February 17 | |
| before breakfast | neg |
| after breakfast | ¼ |
| before lunch | |
| after lunch | ¼ |
| before supper | ¼ |
| after supper | |
| before bed | neg |
| Tuesday, February 18 | |
| before breakfast | neg |
| after breakfast | ¼ |
| before lunch | neg |
| after lunch | neg |
| before supper | |
| after supper | ¼ |
| before bed | ¼ |
| Wednesday, February 19 | |
| before breakfast | ¼ (forgot) |
| after breakfast | ¼ (raisins) |
| before lunch | ¼ |
| after lunch | neg |
| before supper | |
| after supper | |
| before bed | ¼ |
| Thursday, February 20 | |
| before breakfast | neg |
| after breakfast | |
| before lunch | ¼ |
| after lunch | neg |
| before supper | neg |
| after supper | ¼ |
| before bed | neg |
| Friday, February 21 | |
| before breakfast | neg |
| after breakfast | neg |
| before lunch | |
| after lunch | neg |
| before supper | |
| after supper | |
| before bed | neg |
| Saturday, February 22 | |
| before breakfast | neg |
| after breakfast | |
| before lunch | neg |
| after lunch | |
| before supper | neg |
| after supper | ¼ |
| before bed | |
| Sunday, February 23 | |
| before breakfast | neg |
| after breakfast | |
| before lunch | neg |
| after lunch | |
| before supper | neg |
| after supper | neg |
| before bed | |
| Monday, February 24 | |
| before breakfast | neg |
| after breakfast | ¼ |
| before lunch | |
| after lunch | neg |
| before supper | |
| after supper | |
| before bed | ¼ |
| Tuesday, February 25 | |
| before breakfast | neg |
| after breakfast | ¼ |
| before lunch | |
| after lunch | |
| before supper | neg |
| after supper | neg |
| before bed | |
| Wednesday, February 26 | |
| before breakfast | neg |
| after breakfast | |
| before lunch | neg |
| after lunch | neg |
| before supper | |
| after supper | ¼ |
| before bed | ¼ |
| Thursday, February 27 | |
| before breakfast | neg |
| after breakfast | |
| before lunch | |
| after lunch | ¼ |
| before supper | |
| after supper | ¼ |
| before bed | neg |

-continued

| | |
|---|---|
| Friday, February 28 | |
| before breakfast | neg |
| after breakfast | |
| before lunch | ⅟₄ |
| after lunch | neg |
| before supper | |
| after supper | |
| before bed | neg |
| Saturday, February 28 | |
| before breakfast | med |
| after breakfast | ⅟₄ |
| before lunch | |
| after lunch | med |
| before supper | neg |
| after supper | ⅟₄ |
| before bed | |
| Sunday, March 1 | took med |
| before breakfast | neg |
| after breakfast | |
| before lunch | med - neg |
| after lunch | |
| before supper | med - neg |
| after supper | |
| before bed | med - ⅟₄ |
| Monday, March 2 | aspirin |
| before breakfast | med |
| before lunch | med - neg |
| before supper | med - neg |
| before bed | med |
| Tuesday, March 3 | |
| before breakfast | neg |
| after breakfast | neg |
| before lunch | neg |
| after lunch | |
| before supper | ⅟₄ |
| after supper | |
| before bed | neg |
| Wednesday, March 4 | medication |
| before breakfast | neg |
| after breakfast | |
| before lunch | med |
| after lunch | |
| before supper | aspirin |
| after supper | med |
| before bed | med - neg |
| Thursday, March 5 | |
| before breakfast | neg |
| after breakfast | |
| before lunch | |
| after lunch | |
| before supper | ⅟₄ |
| after supper | |
| before bed | ⅟₄ |
| Saturday, March 7 | |
| before breakfast | ⅟₄ |
| before lunch | ⅟₄ |
| after supper | ⅟₄ |
| Sunday, March 8 | |
| before breakfast | neg |
| after lunch | neg |
| after supper | ⅟₄ |
| Monday, March 9 | |
| before breakfast | neg |
| after lunch | neg |
| bedtime | neg |

What is claimed:

1. A method for controlling diabetes mellitus in a diabetic patient, comprising
   (a) testing both the blood sugar level and the urine sugar level of the diabetic patient;
   (b) administering insulin before a meal and sugar after a meal as required by the results of the blood and urine sugar tests; and
   (c) repeating steps (a) and (b) as needed:
   wherein the amount of insulin and sugar administered is adjusted daily based on the blood sugar and urine sugar test results to control diabetes mellitus in the diabetic patient
   (d) increasing the insulin dosage as necessary from the response of the patient to blood and urine sugar content of the patient until a urine sugar level below 2% is reached; and decreasing the insulin dosage until a negative urine sugar level content is achieved.

2. The method of claim 1, wherein the blood and urine sugar levels are tested seven times a day.

3. The method of claim 2, wherein the blood and urine sugar levels are tested before each meal, two hours after each meal and at bedtime.

4. A method for controlling diabetes mellitus in a diabetic patient, comprising
   (a) testing both the blood sugar level and the urine sugar level of the diabetic patient seven times a day;
   (b) administering an amount of insulin and sugar supplementation after an initial administration to reach a maximized need, then, in steadily decreasing dosages, decreasing the insulin to about one unit less per dose than the amount which would induce insulin-induced hypoglycemia; and the sugar supplementation is decreased so as to avoid sugar-induced hyperglycemia;
   (c) continuing the reduction in sugar and insulin dose as needed by results of blood and sugar urine tests until the diabetic patient requires no insulin or sugar, and the urine sugar tests will be negative and the blood sugar tests will be about normal.

5. The method of claim 2, wherein the sugar administered is a simple sugar.

6. A method for reducing or eliminating the dependency of a diabetic patient whose diabetes is out-of-control on administered insulin, comprising
   administering insulin to an out-of-control diabetic patient;
   increasing the insulin dosage as necessary from the response of the patient to blood and urine sugar tests to a maximum while monitoring the blood and urine sugar content of the patient until a urine sugar level below 2% is reached; and
   decreasing the insulin dosage until a negative urine sugar level content and an insulin requirement of zero is achieved;
   wherein sugar is administered in relation to the insulin at dosages in which hypoglycemia is avoided while not causing hyperglycemia.

7. A method of treating a diabetic patient whose diabetes is out-of-control said patient's pancreas being suppressed, exhausted or both comprising
   administering insulin to an out-of-control diabetic patient;
   increasing the insulin dosage as necessary to a maximum that is required by the patient's progress until pancreatic activity is increased as indicated by increased production of insulin; and
   reducing the dosages of administered insulin while monitoring the blood and urine sugars as the pancreas function increasingly takes over by steadily increasing its own insulin production to meet the needs of the patient.

8. A method of treating a diabetic patient, avoiding the onset of insulin-induced hypoglycemia and thereby the damage caused by administering insulin to said diabetic patient, said method comprising (a) testing both the blood sugar level and the urine sugar level of the diabetic patient;

(b) administering insulin before a meal and sugar after a meal as required by the results of the blood and urine sugar tests; and (c) repeating steps (a) and (b) as needed:

wherein the amount of insulin and sugar administered is adjusted daily based on the blood sugar and urine sugar test results to avoid the onset of insulin-induced hypoglycemia in the diabetic patient (d) increasing the insulin dosage as necessary from the response of the patient to blood and urine sugar content of the patient until a urine sugar level below 2% is reached; and decreasing the insulin dosage until a negative urine sugar level content is achieved.

9. A method of making diabetes mellitus progressively milder in a diabetic patient, comprising (a) testing both the blood sugar level and the urine sugar level of the diabetic patient;

(b) administering insulin before a meal and sugar after a meal as required by the results of the blood and urine sugar tests; and (c) repeating steps (a) and (b) as needed: and progressively reducing both in insulin and sugar administered based on the blood and urine sugar tests as the diabetes is reduced to a progressively milder state;

wherein the amount of insulin and sugar administered is adjusted daily based on both the blood sugar and urine sugar test results to make the diabetes mellitus progressively milder (d) increasing the insulin dosage as necessary from the response of the patient to blood and urine sugar content of the patient until a urine sugar level below 2% is reached; and decreasing the insulin dosage until a negative urine sugar level content is achieved.

10. A method of treating diabetes mellitus to a compensated state in a diabetic patient, comprising (a) testing both the blood sugar level and the urine sugar level of the diabetic patient;

(b) administering insulin before a meal and sugar after a meal as required by the results of the blood and urine sugar tests; and (c) repeating steps (a) and (b) as needed: and wherein the amount of insulin and sugar administered is adjusted daily based on both the blood sugar and urine sugar test results to treat diabetes mellitus to a compensated state (d) increasing the insulin dosage as necessary from the response of the patient to blood and urine sugar content of the patient until a urine sugar level below 2% is reached; and decreasing the insulin dosage until a negative urine sugar level content and an insulin requirement of zero is achieved.

11. A method of treating a diabetic patient, avoiding the onset of iatrogenic hyperinsulinaemia in said diabetic patient, comprising (a) testing both the blood sugar level and the urine sugar level of the diabetic patient;

(b) administering insulin before a meal and sugar after a meal as required by the results of the blood and urine sugar tests; and (c) repeating steps (a) and (b) as needed:

wherein the amount of insulin and sugar administered is adjusted daily based on both the blood sugar and urine sugar test results to avoid the onset of iatrogenic hyperinsulinaemia (d) increasing the insulin dosage as necessary from the response of the patient to blood and urine sugar content of the patient until a urine sugar level below 2% is reached; and decreasing the insulin dosage until a negative urine sugar level content and an insulin requirement of zero is achieved.

12. A method of claim 7, wherein the administration of insulin, sugar of both proceeds according to the following:

| Test time | Insulin involved |
| --- | --- |
| Before breakfast | The evening NPH |
| 2 hours after breakfast | The morning regular |
| Before lunch | The morning regular |
| 2 hours after lunch | The before lunch regular and the morning NPH |
| Before supper | The morning NPH and the before lunch regular |
| 2 hours after supper | The before supper regular and the morning NPH |
| Bedtime | The before supper regular and the evening NPH. |

13. A method of claim 8, wherein the administration of insulin, sugar or both proceeds according to the following:

| Test time | Insulin involved |
| --- | --- |
| Before breakfast | The evening NPH |
| 2 hours after breakfast | The morning regular |
| Before lunch | The morning regular |
| 2 hours after lunch | The before lunch regular and the morning NPH |
| Before supper | The morning NPH and the before lunch regular |
| 2 hours after supper | The before supper regular and the morning NPH |
| Bedtime | The before supper regular and the evening NPH. |

14. A method of claim 9, wherein the administration of insulin, sugar or both proceeds according to the following:

| Test time | Insulin involved |
| --- | --- |
| Before breakfast | The evening NPH |
| 2 hours after breakfast | The morning regular |
| Before lunch | The morning regular |
| 2 hours after lunch | The before lunch regular and the morning NPH |
| Before supper | The morning NPH and the before lunch regular |
| 2 hours after supper | The before supper regular and the morning NPH |
| Bedtime | The before supper regular and the evening NPH. |

15. A method of claim 10, wherein the administration of insulin, sugar or both proceeds according to the following:

| Test time | Insulin involved |
| --- | --- |
| Before breakfast | The evening NPH |
| 2 hours after breakfast | The morning regular |
| Before lunch | The morning regular |
| 2 hours after lunch | The before lunch regular and the morning NPH |
| Before supper | The morning NPH and the before lunch regular |
| 2 hours after supper | The before supper regular and the morning NPH |

-continued

| Test time | Insulin involved |
|---|---|
| Bedtime | The before supper regular and the evening NPH. |

16. The method of claim 12, wherein the blood and urine sugar levels are tested about seven times a day.

17. The method of claim 13, wherein the blood and urine sugar levels are tested about seven times a day.

18. The method of claim 14, wherein the blood and urine sugar levels are tested about seven times a day.

19. The method of claim 15, wherein the blood and urine sugar levels are tested about seven times a day.

* * * * *